United States Patent [19]

Southgate et al.

[11] 4,446,146

[45] May 1, 1984

[54] β-LACTAM CONTAINING COMPOUNDS, THEIR PREPARATION AND USE

[75] Inventors: Robert Southgate, Warnham; Terence C. Smale, Epsom Downs; Roger J. Ponsford, Horsham, all of England

[73] Assignee: Beecham Group Limited, England

[21] Appl. No.: 59,463

[22] Filed: Jul. 20, 1979

[30] Foreign Application Priority Data

Jul. 26, 1978 [GB] United Kingdom ............... 31223/78
Jan. 6, 1979 [GB] United Kingdom ................ 7900503

[51] Int. Cl.³ .................... A61K 31/40; C07D 487/04
[52] U.S. Cl. ............................ 424/274; 260/245.2 T; 260/239 A
[58] Field of Search ................ 424/270; 260/245.2 T, 260/245.2 R

[56] References Cited

U.S. PATENT DOCUMENTS

| | | | |
|---|---|---|---|
| 4,141,986 | 2/1979 | Cassidy et al. | 424/274 |
| 4,162,304 | 7/1979 | Box et al. | 260/245.2 T |
| 4,162,323 | 7/1979 | Kahan | 424/274 |
| 4,168,268 | 9/1979 | Dalla et al. | 260/245.2 T |
| 4,168,314 | 9/1979 | Christensen et al. | 260/245.2 |
| 4,172,895 | 10/1979 | Christensen et al. | 260/245.2 |
| 4,252,722 | 2/1981 | Melillo et al. | 260/245.2 T |
| 4,255,441 | 3/1981 | Ponsford et al. | 260/245.2 T |
| 4,263,314 | 4/1981 | Ponsford et al. | 260/245.2 T |
| 4,347,367 | 8/1982 | Christensen et al. | 260/245.2 T |

FOREIGN PATENT DOCUMENTS 1467413 3/1977 United Kingdom .
1489235 10/1977 United Kingdom .

*Primary Examiner*—Mary C. Lee
*Attorney, Agent, or Firm*—Jacobs & Jacobs

[57] ABSTRACT

The compounds of the formula (II):

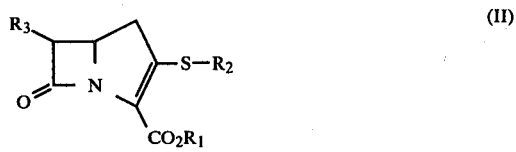

wherein $R_1$ is a group such that $CO_2R_1$ is a carboxylic acid group or a salt or ester thereof; $R_2$ is a group of the sub-formula (a) or (b):

$$-CR_4=C(R_5) NH.CO_nR_6 \qquad (a)$$

$$-CR_7=C(R_8)R_9 \qquad (b)$$

wherein $R_4$ is a hydrogen atom or a lower alkyl group; $R_5$ is a hydrogen atom or a lower alkyl group; $R_6$ is a lower alkyl, phenyl, fluorophenyl, chlorophenyl, bromophenyl or benzyl group; and n is 1 or 2; $R_7$ is a hydrogen or a lower alkyl group; $R_8$ is a hydrogen atom or a lower alkyl group; $R_9$ is a hydrogen atom or a lower alkyl or phenyl group; $R_3$ is a group of the sub-formula (c):

$$CR_{10}R_{11}R_{12} \qquad (c)$$

wherein $R_{10}$ is a hydrogen atom or a hydroxyl or O.-CO.$R_{13}$ or O.CO.O$R_{13}$ group where $R_{13}$ is a lower alkyl, phenyl, benzyl, fluorobenzyl, chlorobenzyl, bromobenzyl, lower alkoxybenzyl or nitrobenzyl group; $R_{11}$ is a hydrogen atom or a lower alkyl group; $R_{12}$ is a hydrogen atom or a lower alkyl group; said compounds being in the form of R,S-mixture at C-5: are antibacterial agents. Their use and a process for their preparation is described.

74 Claims, No Drawings

β-LACTAM CONTAINING COMPOUNDS, THEIR PREPARATION AND USE

The present invention relates to β-lactam containing compounds, to their preparation and to their use in antibacterial pharmaceutical compositions.

British Pat. Nos. 1,467,413, 1,489,235 and 1,483,142 disclose that the naturally occurring compounds of the formula (I):

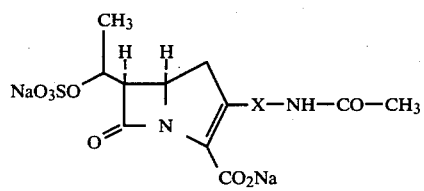

wherein X is —S—CH=CH—, —S—CH$_2$—CH$_2$— or —SO—CH=CH— possess useful antibacterial properties. We have now found that a distinct class of synthetic antibacterial agents which contains a 62-lactam ring fused to a pyrroline ring may be prepared synthetically.

Belgian Pat. No. 864,570 discloses compounds analogous to those of the Formula (I) containing a hydroxy group in place of the sodium sulphate group.

The present invention provides the compounds of the formula (II):

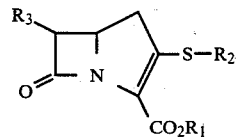

wherein $R_1$ is a group such that $CO_2R_1$ is a carboxylic acid group or a salt or ester thereof; $R_2$ is a group of the sub-formula (a) or (b):

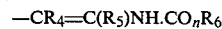

—CR$_4$=C(R$_5$)NH.CO$_n$R$_6$  (a)

—CR$_7$=C(R$_8$)R$_9$  (b)

wherein $R_4$ is a hydrogen atom or a lower alkyl group; $R_5$ is a hydrogen atom or a lower alkyl group; $R_6$ is a lower alkyl, phenyl, fluorophenyl, chlorophenyl, bromophenyl or benzyl group; and n is 1 or 2; $R_7$ is a hydrogen or a lower alkyl group; $R_8$ is a hydrogen atom or a lower alkyl group; $R_9$ is a hydrogen atom or a lower alkyl or phenyl group; $R_3$ is a group of the sub-formula (c):

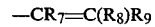

CR$_{10}$R$_{11}$R$_{12}$  (c)

wherein $R_{10}$ is a hydrogen atom or a hydroxyl or O.-CO.R$_{13}$ or O.CO.OR$_{13}$ group where $R_{13}$ is a lower alkyl, phenyl, benzyl, fluorobenzyl, chlorobenzyl, bromobenzyl, lower alkoxybenzyl or nitrobenzyl group; $R_{11}$ is a hydrogen atom or a lower alkyl group; $R_{12}$ is a hydrogen atom or a lower alkyl group; said compounds being in the form of R,S-mixture at C-5.

When used herein the term "lower" means a group of up to 3 carbon atoms. Thus lower alkyl includes methyl, ethyl, n-propyl and iso-propyl of which methyl and ethyl are the more suitable values and methyl the preferred value.

Apt groups of the sub-formulae (a) and (b) include those of the sub-formulae (d) and (e) respectively:

—CR$_{14}$=C(R$_{15}$)NH.CO.R$_{16}$  (d)

—CR$_{14}$=C(R$_{15}$)R$_{17}$  (e)

wherein $R_{14}$ is a hydrogen atom or a methyl group; $R_{15}$ is a hydrogen atom or a methyl group; $R_{16}$ is a lower alkyl group; and $R_{17}$ is a hydrogen atom or a lower alkyl or phenyl group. Favourably $R_{14}$ is a hydrogen atom. Most suitably $R_{15}$ is a hydrogen atom. Most suitably $R_{16}$ is a methyl or ethyl group. Most suitably $R_{17}$ is a hydrogen atom or a methyl or phenyl group.

Group of the sub-formula (a) worthy of mention include the acetamidovinyl, acetamidopropenyl and propionamidovinyl groups.

Groups of the sub-formula (b) worthy of mention include the vinyl and styryl groups.

A preferred group of the sub-formula (a) is the acetamidovinyl group.

A preferred group of the sub-formula (b) is the vinyl group.

It will be realized that the compounds of the sub-formulae (a) and (b) may be in either of two geometrical forms about the exocyclic double bond as shown in the sub-formulae (x) and (y) thus:

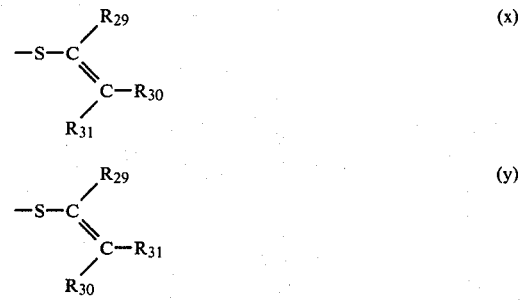

wherein $R_{29}$ is $R_4$ or $R_7$ as hereinbefore defined; $R_{30}$ is $R_5$ or $R_8$ and $R_{31}$ is NHCO$_n$R$_6$ or $R_9$.

Both separated geometrical isomers and mixtures of said isomers are within the scope of this invention.

Apt groups of the sub-formula (c) include those of the sub-formulae (f), (g), (h) and (i):

wherein R₁₈ is a hydrogen atom or a methyl or ethyl group; R₁₉ is a hydrogen atom or a methyl or ethyl group; R₂₀ is a lower alkyl group; R₂₁ is a benzyl, fluorobenzyl, chlorobenzyl, bromobenzyl, lower alkylbenzyl or nitrobenzyl group.

Favourably R₁₈ is a hydrogen atom. Favourably R₂₀ is a methyl or ethyl group. Favourably R₂₁ is a benzyl or p-nitrobenzyl group. Preferably R₂₀ is a methyl group. Preferably R₂₁ is a p-nitrobenzyl group.

Groups of the sub-formula (c) worthy of mention include the methyl, ethyl, n-propyl, α-hydroxyethyl, α-hydroxypropyl, α-acetoxyethyl, α-acetoxypropyl, 2-hydroxy-2-propyl, α-propionoxyethyl and α-p-nitrobenzyloxycarbonyloxyethyl groups.

The compounds of the formula (II) wherein CO₂R₁ is a carboxylic acid group or salt thereof tend to be more active than corresponding esters and are thus particularly suitable. It is most suitable that CO₂R₁ represents a carboxylic acid salt. When R₂ contains an amino group the compound of the formula (II) is zwitterionic. When R₂ does not contain an amino group it is preferred that CO₂R₁ is a carboxylic acid group salted by a pharmaceutically acceptable cation such as those of the alkali or alkaline earth metals or a nontoxic amine. Favoured salts include the sodium and potassium salts.

Compounds of the formula (II) wherein CO₂R₁ is an ester group have activity in their own right but less than the corresponding salts so in general it is preferred that esters of this invention are those which are convertible to a corresponding salt by chemical or biological means.

Suitable R₁ is a group of the sub-formulae (j) (k), (l) or (m):

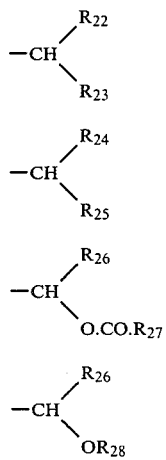

wherein R₂₂ is a hydrogen atom or an alkyl, alkenyl or alkynyl group of up to 3 carbon atoms; R₂₃ is a hydrogen atom or a methyl group; R₂₄ is a phenyl group or a phenyl group substituted by a fluorine, chlorine or bromine atom or a nitro, methyl or methoxyl group; R₂₅ is a hydrogen atom or a phenyl group or a phenyl group substituted by a fluorine, chlorine or bromine atom or a nitro, methyl or methoxyl group; R₂₆ is a hydrogen atom or a methyl group and R₂₇ is a lower alkyl, phenyl or lower alkoxy group or R₂₆ is joined to R₂₇ to form a phthalidyl group; and R₂₈ is a lower alkyl, phenyl, chlorophenyl or nitrophenyl group.

Favourably R₂₂ is a hydrogen atom or a methyl, ethyl or vinyl group. Favourably R₂₃ is a hydrogen atom. Favourably R₂₄ is a phenyl, p-bromophenyl, p-methoxyphenyl or p-nitrophenyl group. Favourably R₂₅ is a hydrogen atom. Favourably R₂₇ is a methyl, t-butyl or ethoxyl group or is joined to R₂₆. Favourably R₂₈ is a methyl group.

Particularly apt groups of the sub-formula (j) include the methyl and ethyl groups.

Particularly apt groups of the sub-formula (k) include the benzyl and p-nitrobenzyl groups.

Particularly apt groups of the sub-formula (l) include the acetoxymethyl, pivaloyloxymethyl, α-ethoxycarbonyloxyethyl and phthalidyl groups.

A particularly apt group of the sub-formula (m) is the methoxymethyl group.

A preferred value for R₁ when CO₂R₁ is an ester group is p-nitrobenzyl.

A further preferred value for R₁ when CO₂R₁ is an ester group is the phthalidyl group.

Thus one particularly apt group of compounds falling within formula (III) is that of the formula (IV):

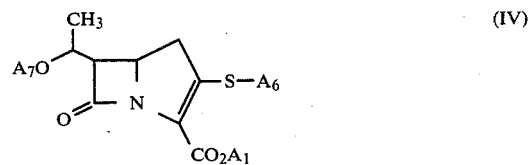

wherein A₁ is as defined in relation to formula (III), A₆ is an acetamidovinyl group and A₇ is a hydrogen atom or an acetyl group.

Aptly CO₂A₁ is a pharmaceutically acceptable salt of a carboxyl group.

Aptly CO₂A₁ is an in vivo hydrolysable ester group such as the phthalidyl ester group.

Aptly CO₂A₁ is a p-nitrobenzyl ester group.

It will be realized that the compounds of the formula (IV) may exist in either of two epimeric forms at C-8 (8R or 8S); these epimers may be separated by conventional means such as fractional crystallisation, countercurrent separation or chromatography. We have found that it is most convenient to separate the C-8 epimers by column chromatography.

The compounds of this invention, for example those of the formulae (II)–(IV) are provided in the form of R,S- mixtures at C5. It is believed that the active isomer from this mixture is that which exemplified in relation to formula (II) has the configuration shown in formula (V):

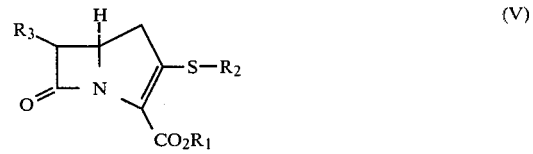

The compounds of the formulae (II)–(V) may have the R—, S— or mixtures of R— and S— configuration at C6. Thus using formula (V) to demonstrate these configurations the compounds shown in formulae (VI) and (VII) are worthy of note:

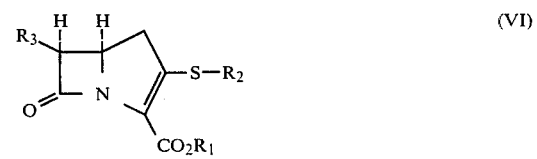

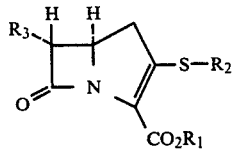

(VII)

The present invention also provides a pharmaceutical composition which comprises a compound of this invention and a pharmaceutically acceptable carrier.

Most suitably the composition will be in unit dosage form and will comprise 25–1000 mg or more usually 50–500 mg of a compound of this invention.

Usually the compositions of this invention will be in a form suitable for oral or injectable administration.

Favourably the compound used in the composition will be a salt or in-vivo hydrolysable ester. Thus favourably the compound may be in the form of a sodium or potassium salt or phthalidyl ester or the like.

The composition of this invention may beneficially also comprise a penicillin or a cephalosporin. Certain particularly suitable penicillins for use in these compositions include amoxycillin trihydrate and sodium amoxycillin.

The compositions may be prepared in conventional manner for the preparation of $\beta$-lactam antibiotics and may employ conventional carriers such as diluents, disintegrants, lubricants, colourants, flavourants and the like.

The present invention also provides a method of treating bacterial infections in humans or domestic mammals which comprises the administration of a composition of this invention.

The compounds of the present invention may be prepared by reaction sequences such as those outlined in Schemes 1, 2 and 3. In the Schemes PNB means paranitrobenzyl. Although Schemes 1 and 2 show the preparation of compounds with a 6-CH(CH$_3$)OH group via compounds with a 6-CH(CH$_3$)OCOPNB group it should be appreciated that other moieties R$_3$ may be included at the 6-position, e.g. one of the sub-formulae (i), (j), (k) or (l) as hereinbefore defined.

SCHEME 1

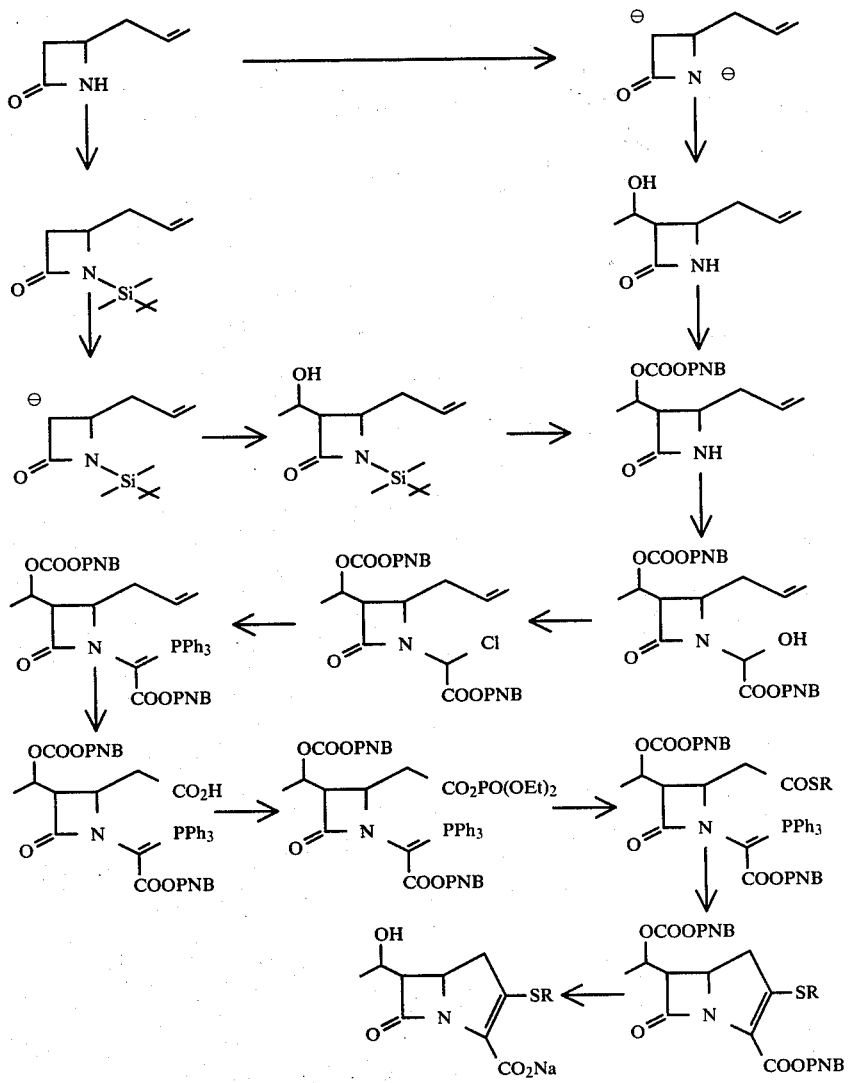

SCHEME 2
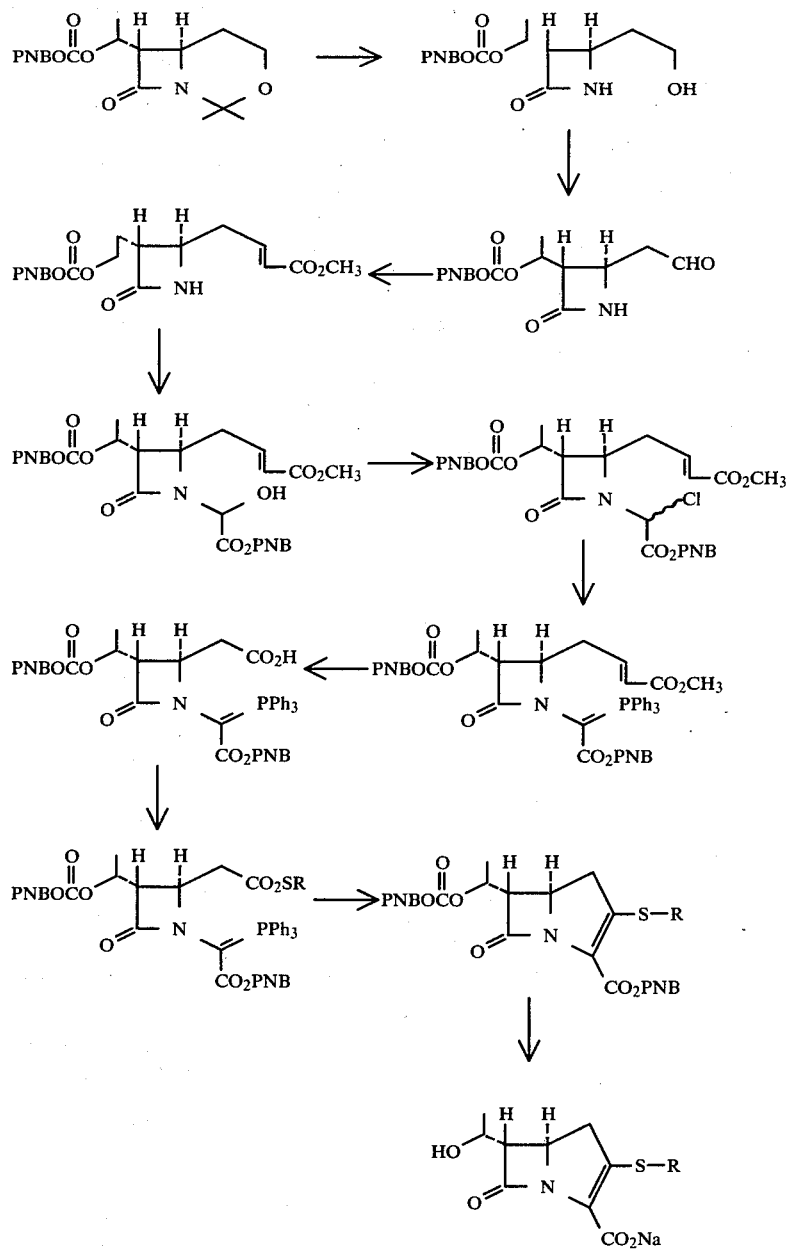
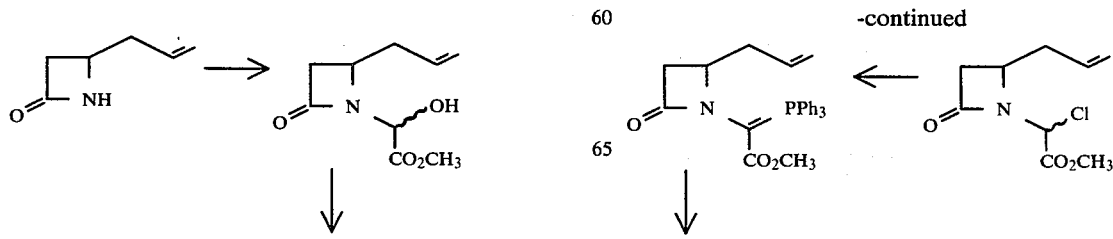

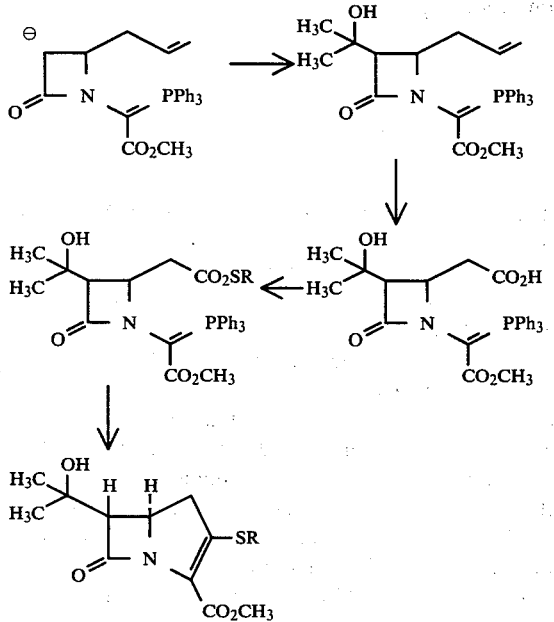

The present invention also provides a process for the preparation of the compounds of this invention which process comprises the ring closing elimination of the elements of triphenylphosphine oxide from an ester of a compound of the formula (VIII):

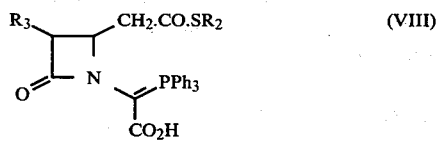

wherein $R_2$ and $R_3$ are as defined in relation to formula (II) and thereafter if desired (a) isolating the ester thus produced, (b) where desired de-esterifying a cleavable ester to form a free acid or its salt, (c) optionally converting the salt so formed into a free acid or optionally converting the acid so formed into a salt, and (d) optionally converting a salt into an alternative ester.

Any reactive moiety present in $R_2$ or $R_3$ may be protected during the ring closure if desired, for example as as p-nitrobenzyloxycarbonyl derivative.

The ring closure in normally brought about by heating the ester of the compound of the formula (VIII) in an inert solvent; for example temperatures of 90°–120° C. and more suitably 100°–110° C. may be employed in a solvent such as toluene or the like. The reaction is best carried out under dry conditions under an inert gas.

The ester of the compound (II) produced may be isolated by any standard method such as fractional crystallisation, counter current separation or chromatography. We have found that it is most convenient to separate the desired product by column chromatography.

Any convenient ester may be used in the process of this invention. Since it is frequently desirable to form a salt of compounds (II), the ester employed is preferably one which is readily converted to the parent acid or its salt by mild methods of hydrogenolysis. In a further aspect therefore the invention includes a process for preparing a salt or free acid of a compound (II) which process comprises de-esterifying an ester of a compound of formula (II). Particularly suitable esters for use in this process include benzyl esters, optionally substituted in the para position by a lower alkoxy, or nitro group or a halogen atom.

A preferred ester for use in this process is the p-nitrobenzyl ester.

Esters of compounds (II) may be de-esterified by conventional methods of hydrogenolysis.

Suitable methods include hydrogenation in the presence of a transition metal catalyst. The pressure of hydrogen used in the reaction may be low, medium or high but in general an approximately atmospheric or slightly super-atmospheric pressure of hydrogen is preferred. The transition metal catalyst employed is preferably palladium on charcoal or on calcium carbonate. The hydrogenation may be effected in any inert solvent in which the ester is soluble such as aqueous dioxan or the like. If this hydrogenation is carried out in the presence of a base then a salt of compounds (II) is produced. Suitable bases for inclusion include $NaHCO_3$, $KHCO_3$, $Na_2CO_3$, $K_2CO_3$, $CaCO_3$, $MgCO_3$, $LiHCO_3$, $NH_4OCOCH_3$ and the like. If no base is present then hydrogenation leads to the preparation of an acid within formula (II) which may then be neutralised if desired to yield a salt. Suitable bases which may be used to neturalise acids within formula (II) include LiOH, NaOH, NaHCO$_3$, KOH, Ca(OH)$_2$ and Ba(OH)$_2$.

The salts of acids (II) may be converted to esters in conventional manner, for example by reaction with a reactive halide such as bromophthalide in solution in dimethylformamide or like solvent.

The substituent group or groups within the groups $R_2$ and $R_3$ in the compounds of formula (II) may be varied by conventional reactions. Thus for example when a substituent is a nitro group it may be reduced in a conventional manner to an amino group, for example by catalysed hydrogenation. Similarly an amino group may be acylated to give a substituted amido group, for example by treatment with an acyl halide in the presence of an organic base. Substituents such as NHCO$_2$p-nitrobenzyl or OCO$_2$p-nitrobenzyl may be converted to an amino or hydroxyl group for example by hydrogenolysis.

The ester of the compound of the formula (VIII) may be prepared by the reaction of a corresponding ester of a compound of the formula (IX):

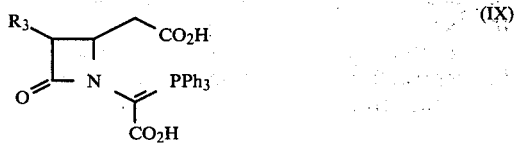

wherein $R_3$ is as defined in relation to formula (II) with a diloweralkylphosphorochloridate or thionylchloride and a triloweralkylamine followed by reaction with a derivative of the formula (X):

$$L^{\oplus}{}^{\ominus}S{-}R_2 \qquad (X)$$

where $L^{\oplus}$ is a sodium, silver or thallium I cation or an ammonium ion substituted by up to three lower alkyl groups, and $R_2$ is as defined in relation to formula (II). $L^{\oplus}$ may also be a lithium cation.

When $L^{\oplus}$ is a substituted ammonium ion, it is preferably a tertiary ammonium ion, such as the triethylammonium ion. It is conveniently generated in situ by the reaction of a compound of the formula HSR$_2$ with an amine, preferably a teriary amine.

Preferably L$^\oplus$ is a thallium I cation or a silver cation.

A particularly suitable diloweralkylphosphorochloridate is diethylphosphorochloridate.

A particularly suitable triloweralkylamine is triethylamine.

The reaction is generally carried out in an inert organic solvent such as tetrahydrofuran at a non-extreme temperature such as 0° to 40° C., for example 15°–25° C.

The ester of the compound of the formula (IX) may be prepared by the reaction of the compound of the formula (XI):

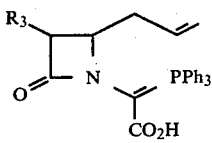

(XI)

wherein R$_3$ is as defined as in relation to formula (II) with ozone in the presence of trifluoroacetic acid followed by m-chloroperbenzoic acid.

The ozonolysis is generally performed at a depressed temperature such as −40° to −80° C., for example about −70° C. and in solution in an inert solvent such as methylene chloride. Excess ozone is removed by flushing with an inert gas and thereafter a solution of the peracid is added to the reaction mixture.

The ester of the compound of the formula (XI) may be prepared from the corresponding ester of a compound of the formula (XII):

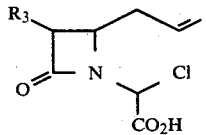

(XII)

wherein R$_3$ is as defined in relation to formula (II) with triphenylphosphine.

This reaction is normally effected in the presence of at least one equivalent of a base of relatively low nucleophilicity such as 2,6-lutidine at an ambient temperature in a dry solvent such as dioxan, tetrahydrofuran or the like.

The ester of the compound of the formula (XII) may be prepared from the corresponding ester of the carbinol of the formula (XIII):

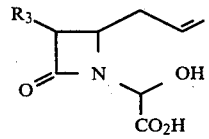

(XIII)

wherein R$_3$ is as defined in relation to formula (II) by reaction with thionyl chloride.

This reaction is also normally effected in the presence of at least one equivalent of a base of relatively low nucleophilicity in a dry solvent such as dioxan or tetrahydrofuran but in this instance the reaction is performed at a depressed temperature, for example −30° to −10° C.

The preceding carbinol may be prepared by the reaction of a compound of the formula (XIV):

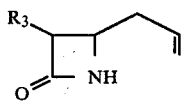

(XIV)

wherein R$_3$ is as defined in relation to formula (II) with a glyoxylic acid ester.

Normally this reaction is carried out in an inert solvent at an elevated temperature, for example in dry benzene under reflux.

The esters of the compounds of the formula (XIII) may also be prepared by esterification of a salt of the compound of the formula (XIII) in conventional manner. Suitable methods include the reaction of alklai metal salt such as a sodium or potassium salt with a relative halide or sulphonate ester such as a bromide, chloride, mesylate, tosylate or the like. Such esterification may be carried out under conventional conditions, for example in dimethylformamide at room temperature.

The salt of compound of the formula (XIII) may be prepared by neutralisation of the acid of the formula (XIII), for example with an alkali metal carbonate or bicarbonate, for example sodium or potassium carbonate.

The compound of formula (XIII) may be prepared by the reaction of glyoxylic acid with the compounds of the formula (XIV) as hereinbefore defined.

The compound of the formula (XIV) may be prepared by the reaction of the compound of the formulae (XVa) or (XVb):

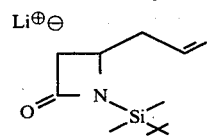
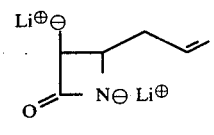

(XVa)          (XVb)

with a compound of the formula (XVI) or (XVII):

R$_{11}$.CO.R$_{12}$ (XVI)

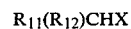

R$_{11}$(R$_{12}$)CHX (XVII)

wherein R$_{11}$ and R$_{12}$ are as defined in relation to formula (II) and X is a chlorine, bromine or iodine atom; and thereafter acylating the product formed by reaction with the compound of the formula (XVI) if desired.

Generally the compound of the formula (XVb) is generated and utilized in situ. Thus 4-allyl-azetidin-2-one may be treated with two equivalents of n-butyl lithium in tetrahydrofuran at a low temperature. The dianion may be quenched by the addition of a compound of the formula (XVI) or (XVII).

The compound of the formula (XVI) also may be prepared by the reaction of the compound of the formula (XVa):

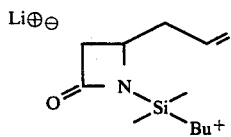 (XVa)

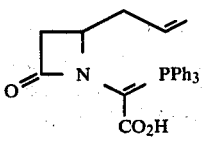 (XX)

with a compound of the formula (XVI) or (XVII) as hereinbefore defined.

Generally the compound of the formula (XVa) is generated and utilised in situ. Thus 4-allyl-1-t-butyl-dimethylsilylazetidin-2-one may be treated with two equivalents of n-butyl lithium in tetrahydrofuran at a low temperature. The anion may be quenched by the addition of a compound of the formula (XVI) or (XVII). 4-Allyl-1-t-butyldimethysilylazetidin-2-one may be prepared by the reaction of 4-allylazetidin-2-one with t-butyldimethylsilyl chloride and triethylamine in an inert solvent. The t-butyldimethylsilyl protecting group may be removed, when necessary, on treatment with potassium fluoride and a crown ether in an inert solvent.

The esters of the compound of the formula (IX) may also be prepared by the ozonolysis of an ester of a compound of the formula (XVIII):

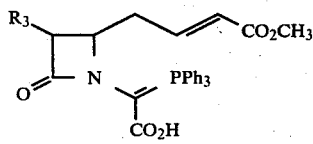 (XVIII)

wherein $R_3$ is as defined in relation to formula (II) followed by m-chloroperbenzoic acid.

the ozonolysis is generally performed in the presence of trifluoroacetic acid in methylene chloride at $-70°$ C.

The ester of the compound of the formula (XVIII) may be prepared in a manner analogous to that described for the sequence (XIII)→(XII)→(XI), supra, namely treatment of the N-unsubstituted compound with a glyoxylic acid ester, chlorination with thionyl chloride and treatment with triphenylphosphine, as shown on Scheme 2, supra. The N-unsubstituted compound in turn may be obtained from a compound of the formula (XIX):

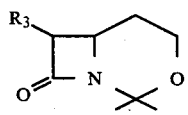 (XIX)

or the corresponding spirocyclohexyl analogue wherein $R_3$ is as defined for formula II, by hydrolysis as with aqueous acetone and a small quantity of a mineral acid such as sulfuric acid, followed by oxidation of the resulting 2-hydroxypropyl compound to the corresponding aldehyde, followed by treatment with carbomethoxymethylenephosphorane as shown on Scheme 2, supra.

Esters of the compound of the formula (XI) may also be prepared by the reaction of an ester of a compound of the formula:

with a compound of the formula (XVI) or (XVII) as hereinbefore defined in the presence of a strong base and thereafter if desired acylating the product formed by reaction with a compound of the formula (XVI).

Strong bases for use in this reaction are those of low nucleophilicity such as lithium N,N-isopropylcyclohexylamide and similar reagents. The reaction is generally carried out in tetrahydrofuran at a low temperature such as $-80°$ C.

The compound of the formula (XIII) may be prepared from the corresponding chloro compound which in turn may be prepared from the corresponding N—H compound by processes analogous to that for the sequence (XIV)-(XIII)-(XII) as hereinbefore described.

Isomerisation of terminal moieties of sub-formula (b) may be effected using a mercuric salt in the presence of an inert solvent. The presence of a buffering agent to control the pH of this isomerisation reaction has proved advantageous. A suitable agent for this purpose is calcium carbonate.

Preferably this isomerisation reaction is carried out on a compound of the formula (II) wherein $R_1$ is an esterifying group, since separation of the geometric isomer of the formula (II) from other materials may then generally be achieved more easily than when the compounds contain a free or salted acid group.

The solvent used in the process will be selected primarily on the basis of the solubility of the compound (II) therein, a large number of solvents being suitable; for example, acetonitrile, acetone, dichloromethane, chloroform and water. A suitable solvent mixture is acetonitrile-water.

The reaction is generally carried out at a moderate temperature, for example, from $-30°$ to $+50°$ C., room temperature being particularly convenient, when the reaction is generally complete in a few minutes.

European Patent Application Publication No. 0000828 should be consulted for descriptions of the preparation of intermediates. European Patent Application Nos. 0001627 and 0001628 may also be referred to. Other helpful disclosures include French Patent Application Publication Nos. 2392996 and 2371449. Further procedures for the preparation of intermediates are found in European Patent Application No. 78300873.3 and U.S. Ser. No. 004,896 which are also incorporated herein by reference.

DESCRIPTION 1

Acetoacetyl-2,2'-dimethyltetrahydro-1,3-oxazine 2,2'-Dimethyltetrahydro-1,3-oxazine (4.56 g) was dissolved in ethanol (50 ml) and diketene (freshly distilled) (3.36 g) added at 5°. The mixture was stirred at R.T. for three hours. Evaporation of the solvent and chromatography yielded acetoacetyl-2,2-dimethyltetrahydro-1,3-oxazine (4 g; 60%) as an oil.

Similarly acetoacetyl-2,2'-spirocyclohexyltetrahydro-1,3-oxazine was prepared.

DESCRIPTION 2

Acetodiazoacetyl-2,2′dimethyltetrahydro-1,3-oxazine

Acetoacetyl-2,2′-dimethyltetrahydro-1,3-oxazine (3.00 g) was dissolved in acetonitrile (25 ml) and treated with Et₃N (1.5 g) and tosyl azide (4.5 g; 1.5 equivs). The mixture was stirred at R.T. overnight, the solvent evaporated and the residue chromatographed to yield acetodiazoacetyl-2,2-dimethyltetrahydro-1,3-oxazine as an oil (3 g, 89%).

Similarly acetodiazoacetyl-2,2′-spirocyclohexyltetrahydro-1,3-oxazine was prepared.

DESCRIPTION 3

7α-(Acetyl)-2,2′dimethyl-3-oxa-8-oxo-1-aza-bicyclo [4.2.0]octane

Acetodiazoacetyl-2,2′-dimethyltetrahydro-1,3-oxazine (2 g) was dissolved in freshly distilled ether (700 ml) and degassed at −60° for ten minutes. Photolysis of the solution at −60° using a Hanovia 450 w medium pressure mercury lamp and pyrex reaction vessel over 8 h while the solution gradually warmed to −20° gave 7α-acetyl-2,2-dimethyl-3-oxa-8-oxo-1-aza-bicyclo [4.2.0] as an oil after chromatography (1.2 g; 55%).

Similarly 7α-(acetyl)-2,2′-spirocyclohexyl-3-oxa-8-oxo-1-azabicyclo[4.2.0]octane was prepared.

In an improved process acetodiazoacetyl-2,2′-spirocyclohexyltetrahydro-1,3-oxazine (0.56 g) was dissolved in chloroform (20 ml) and treated with rhodium (II) acetate (0.2 g). The mixture was stirred at room temperature for four hours, filtered and the filtrate evaporated. Chromatography of the residual oil on Mercle Kieselgel 60 (<230 mesh) using ethyl acetate/petrol (60°–80°) gave 7α-(acetyl)-2,2′-spirocyclohexyl-3-oxa-8-oxo-1-azabicyclo[4.2.0]octane as an oil which solidified when left standing at 0° overnight (0.37 g: 76%).

DESCRIPTION 4

7α-(1-Hydroxyethyl)-2,2′-dimethyl-3-oxa-8-oxo-1-azabicyclo[4.2.0]octane

7α-Acetonyl-2,2-dimethyl-3-oxa-8-oxo-1-azabicyclo [4.2.0]octane (0.99 g) was dissolved in ethanol (10 ml) and NaBH₄ (0.1 g) in ethanol (5 ml) was added at 0°. The reaction was stirred at 0° for 30 min., the solvent evaporated and the residue chromatographed to yield 7α-(1-Hydroxyethyl)-2,2-dimethyl-3-oxa-8-oxo-1-azabicyclo [4.2.0]octane (0.75 g; 75%).

Similarly 7α-(1-hydroxyethyl)-2,2′-spirocyclohexyl-3-oxa-8-oxo-1-azabicyclo[4.2.0] was prepared.

DESCRIPTION 5

7α-(1-Phenoxyacetylethyl)-2,2′-dimethyl-3-oxa-8-oxo-1-azabicyclo[4.2.0]octane

7α-(1-Hydroxyethyl)-2,2-dimethyl-3-oxa-8-oxo-1-azabicyclo[4.2.0]octane (500 mg) was dissolved in methylene chloride (10 ml) and cooled to −5°. Pyridine (230 mg) was added followed by phenoxyacetyl chloride (430 mg). The reaction was stirred at 0° for two hours, the solution washed with 20% citric acid (3×10 ml) and 3% NaHCO₃ (3×10 ml) and dried over MgSO₄. Evaporation of the solvent and chromatography gave 7α-(1-phenoxyacetylethyl)-2,2-dimethyl-3-oxa-8-oxo-1-azabicyclo[4.2.0]octane as an oil (420 mg; 50%).

DESCRIPTION 6

7α-(1R-Hydroxyethyl)-2,2′-spirocyclohexyl-8-oxo-3-oxa-1-azabicyclo [4.2.0]octane (Stereospecific reduction)

7α-(Acetyl)-2,2′-spirocyclohexyl-3-oxo-1-azabicyclo [4.2.0]octane (0.237 g) was dissolved in dry tetrahydrofuran (20 ml) and treated with a solution of potassium selectride [0.5 m solution in tetrahydrofuran] (2.2 ml), the reaction was stirred at R.T. for two hours and water (10 ml) was added. The solvent was evaporated and the aqueous phase extracted with ethyl acetate (2×10 ml). The extract was dried (MgSO4) and evaporated. The product (single isomer) crystallised from ether as a colourless solid m.p. 145°–7°.

DESCRIPTION 7

5(R, S), 6(S, R) Benzyl 6-(2-hydroxyprop-2-yl)-3-phenylthio-7-oxo-1-azabicyclo[3,2,0]hept-2-ene-2-carboxylate (i)

4-Allyl-3-(2-hydroxyprop-2-yl)-1-(1-benzyloxycarbonyl-1-triphenylphosphoranylidenemethyl)azetidin-2-one A solution of N-isopropylcyclohexylamine (0.60 g) in dry tetrahydrofuran (10 cm³) was stirred under argon and cooled to −78°. This was treated with a 2.5 M solution of n-butyl lithium in n-hexane (1.70 cm³). After ten minutes, a solution of 4-allyl-1-(1-benzyloxycarbonyl-1-triphenylphosphoranylidenemethyl) azetidin-2-one (1.00 g) in dry tetrahydrofuran (15 cm³) was added. Five minutes were allowed for the formation of the C(3) carbanion which was then quenched by the addition of dry acetone (0.71 cm³). The cooling bath was then removed and the mixture stirred for a further ten minutes before it was neutralised with acetic acid (0.56 g). The solvent was evaporated under reduced pressure and the residue chromatographed on silica gel 60 (<230 mesh), eluting with ethyl acetate/60°–80° petroleum ether mixtures grading from 1:1 to 7:3. this gave the two separate isomers of 4-allyl-3-(2-hydroxyprop-2-yl)-1-(1-benzyloxycarbonyl-1-triphenylphosphoranylidenemethyl)azetidin-2-one(0.30 g 27%) and (0.22 g, 20%); $\nu_{max}$(CHCl₃) 3000, 1735 and 1620 cm⁻¹.

(ii)

4-Carboxymethyl-3-(2-hydroxyprop-2-yl)-1-(1-benzyloxycarbonyl-1-triphenylphosphoranylidenemethyl)azetidin-2-one The trans isomer of 4-allyl-3-(2-hydroxyprop-2-yl)-1-(1-benzyloxycarbonyl-1-triphenylphosphoranylidenemethyl) azetidin-2-one (0.74 g) in dry dichloromethane (40 cm³) was treated with trifluoroacetic acid (0.15 g). The solution was cooled to −78° under argon and ozone was then passed through the solution until a blue colour developed. The excess ozone was blown off with argon and the solution was treated with m-chloroperbenzoic acid (0.22 g) in dry dichloromethane (70 cm³) and the mixture was stirred at room temperature for three hours. The solvent was evaporated and the resulting solid was chromatographed on silica gel 60 (<230 mesh) eluting with ethyl acetate/ethanol mixtures grading from 1:0 to 1:1. This gave the product as the trifluoracetic acid salt. This product was stirred in ethyl acetate with basic alumina (0.6 g) for ninety minutes. Filtration and evaporation of the solution gave 4-carboxymethyl-3-(2-hydroxyprop-2-yl)-1-(1-benzyloxycarbonyl-1-triphenylphosphoranylidenemethyl)azetidin-2-one (0.42 g, 55%); $v_{max}$(CHCl$_3$) 3450, 3000, 1750, 1690 and 1620 cm$^{-1}$.

(iii)
4-Phenylthiocarbonylmethyl-3-(2-hydroxyprop-2-yl)-1-(1-benzyloxycarbonyl-1-triphenylphosphoranylidenemethyl)azetidin-2-one 4-Carboxymethyl-3-(2-hydroxyprop-2-yl)-1-(1-benzyloxycarbonyl-1-triphenylphosphoranylidenemethyl)azetidin-2-one (0.12 g) in dry tetrahydrofuran (10 cm$^3$) was treated with triethylamine (22 mg) followed by the dropwise addition of diethylphosphorochloridate (38 ml) in dry tetrahydrofuran (2 cm$^3$) under argon, and the mixture was stirred at room temperature for three hours. To the solution was added thallium phenylthiolate (69 mg) and the mixture was stirred at room temperature overnight. Filtration and evaporation under reduced pressure gave a crude product which was chromatographed on silica gel 60 (<230 mesh) eluting with ethyl acetate/60°-80° petroleum ether mixture in the ratio 7:3 to give pure 4-phenylthiocarbonylmethyl-3-(2-hydroxyprop-2-yl)-1-(1-benzyloxycarbonyl-1-triphenylphosphoranylidenemethyl)azetidin-2-one. (85 mg, 61%); $v_{max}$(CHCl$_3$) 3450, 3000, 1740, 1700 and 1620 cm$^{-1}$.

(iv) 5(R,S), 6(S, R) Benzyl
6-(2-hydroxyprop-2-yl)-3-phenylthio-7-oxo-1-azabicyclo[3,2,0]hept-2-ene-2-carboxylate 4-Phenylthiocarbonylmethyl-3-(2-hydroxyprop-2-yl)-1-(1-benzylcarbonyl-1-triphenylphosphoranylidenemethyl) azetidin-2-one (230 mg) in toluene (150 cm$^3$) was refluxed under argon for eight hours, after which the solvent was evaporated under reduced pressure. The crude product was chromatographed on BDH 'Florisil' (60-100 mesh) eluting with a 1:1 ethyl acetate/60°-80° petroleum ether mixture which gave 5(R, S), 6(S, R) benzyl 6-(2-hydroxyprop-2-yl)-3-phenylthio-7-oxo-1-azabicyclo[3,2,0]hept-2-ene-2-carboxylate (25 mg, 18%); $v_{max}$(CHCl$_3$) 3000, 1775 and 1700 cm$^{-1}$; $\lambda_{max}$(EtOH) 318 nm; $\delta$(C$_6$D$_6$), 0.47 (1H, s, OH), 0.87 (3H, s,CH$_3$), 1.06 (3H, s, CH$_3$), 2.20 (2H, d, J 9 Hz, C(4)H$_2$), 2.49 (1H, d, J 3 Hz, C(6)H), 3.62 (1H, dt, J 3 and 9 Hz, C(5)H, 5.12 and 5.30 (2H, ABq, 12 Hz, Benzyl CH$_2$), 6.85-7.50 (10H, m,10 phenyl H). The product crystallised from ethyl acetate/petroleum ether; (m.p. 133°-136°).

DESCRIPTION 8

5(R, S), 6(R, S), and 5(R, S), 6(S, R) Benzyl
6-(1-acetoxyethyl)-3-phenylthio-7-oxo-1-azabicyclo[3,2,0]hept-2-ene-2-carboxylate (i)
4-Allyl-3-(1-hydroxyethyl)-1-(1-benzyloxycarbonyl-1-triphenylphosphoranylidenemethyl)azetidin-2-one A solution of N-isopropylcyclohexylamine (0.60 g) in dry tetrahydrofuran (10 cm$^3$) was stirred under argon and cooled to -78°. This was treated with a 2.5 M solution of n-butyl lithium in n-hexane (1.70 cm$^3$). After ten minutes, a solution of 4-allyl-1-(1-benzyloxycarbonyl-1-triphenylphosphoranylidenemethyl)azetidin-2-one (1.00 g) in dry tetrahydrofuran (15 cm$^3$) was added. Five minutes were allowed for the formation of the C(3) carbanion which was quenched by the addition of acetaldehyde (0.54 cm$^3$).

The mixture was stirred under argon for a further ten minutes before it was neutralised with acetic acid (0.56 g). The solvent was evaporated under reduced pressure and the residue chromatographed on silica gel 60 (<230 mesh) eluting with ethyl acetate/cyclohexane mixtures grading from 1:1 to 1:0. This gave a mixture of one cis and two trans-isomers of 4-allyl-3-(1-hydroxyethyl)-1-(1-benzyloxycarbonyl-1-triphenylphosphoranylidenemethyl)azetidin-2-one (0.71 g, 65%)$v_{max}$(CHCl$_3$) 3000, 1735 and 1620 cm$^{-1}$.

(ii)
4-Allyl-3-(1-acetoxyethyl)-1-(1-benzyloxycarbonyl-1-triphenylphosphoranylidenemethyl)azetidin-2-one A mixture of one cis and two trans-isomers of 4-allyl-3-(1-hydroxyethyl)-1-(1-benzyloxycarbonyl-1-triphenylphosphoranylidenemethyl)azetidin-2-one (5.0 g) in dry dichloromethane (150 cm$^3$) was treated with 4-N,N-dimethylaminopyridine (1.22 g) followed by acetic anhydride (2.27 g) and the solution was stirred overnight at room temperature. The solution was evaporated under reduced pressure and the residue was chromatographed using high performance liquid chromatography, eluting with a 6:4 ethyl acetate/60°-80° petroleum ether mixture. This gave one cis and two trans-isomers of 4-allyl-3-(1-acetoxyethyl)-1-(1-benzyloxycarbonyl-1-triphenylphosphoranylidenemethyl)azetidin-2-one. The yields were the cis isomer (1.10 g, 21%) one trans isomer (0.28 g, 5%) and the other trans isomer (1.23 g, 23%). The cis-isomer crystallised (m.p. 156°-160° decomp). The infra-red spectra of all three isomers were identical; $v_{max}$ (CHCl$_3$) 3000, 1730, 1635 and 1610 cm$^{-1}$.

(iii) cis
4-Carboxymethyl-3-(1-acetoxyethyl)-1-(1-benzyloxycarbonyl-1-triphenylphosphoranylidenemethyl)azetidin-2-one 4-Allyl-3-(1-acetoxyethyl)-1-(1-benzyloxycarbonyl-1-triphenylphosphoranylidenemethyl)azetidin-2-one (0.54 g) in dry dichloromethane (40 cm$^3$) was treated with trifluoroacetic acid (0.7 cm$^3$) and cooled, under argon, to -78°. Ozone was passed through the solution until a blue colour developed. The excess ozone was blown off with argon and the solution was treated with m-chloroperbenzoic acid (0.18 g) in dry dichloromethane (10 cm$^3$), and the solution was stirred at room temperature overnight. The solvent was evaporated under reduced pressure and the residue was chromatographed on silica gel eluting with ethyl acetate/methanol mixtures graded from 1:0 to 4:1 to give the trifluoroacetic acid salt of cis-4-carboxymethyl-3-(1-acetoxyethyl)-1-(1-benzyloxycarbonyl-1-triphenylphosphoranylidenemethyl)azetidin-2-one. The salt was dissolved in ethyl acetate and stirred with basic alumina (0.5 g) at room temperature for one hour. Filtration and evaporation gave 4-carboxymethyl-3-(1-acetoxyethyl)-1-(1-benzyloxycarbonyl-1-triphenylphosphoranylidenemethyl)azetidin-2-one (610 mg); $v_{max}$ (CHCl$_3$) 3400, 3000 and 1730 cm$^{-1}$.

(iv)
Cis-4-Phenylthiocarbonylmethyl-3-(1-acetoxyethyl)-1-(1-benzyloxycarbonyl-1-triphenylphosphoranylidenemethyl)azetidin-2-one Cis-4-carboxymethyl-3-(1-acetoxyethyl)-1-(1-benzyloxycarbonyl-1-triphenylphosphoranylidenemethyl)azetidin-2-one (0.61 g) in dry tetrahydrofuran (50 cm$^3$)

was treated with triethylamine (0.12 g) in dry tetrahydrofuran (1 cm³), and the solution was cooled to 0° under argon. Diethylphosphorochloridate (0.2 g) in dry tetrahydrofuran (20 cm³) was added dropwise, and the solution was stirred for three hours at room temperature under argon. The solution was treated with sodium phenylthiolate (0.13 g) in dry tetrahydrofuran (10 cm³), and the mixture was stirred at room temperature for one hour. Filtration and evaporation under reduced pressure gave a residue which was chromatographed on silica gel 60 (<230 mesh) eluting with a 1:1 ethyl acetate/60°-80° petroleum ether mixture. This gave cis-4-phenylthiocarbonylmethyl-3-(1-acetoxyethyl)-1-(1-benzyloxycarbonyl-1-triphenylphosphoranylidenemethyl)azetidin-2-one (0.30 g, 43%); $\nu_{max}$ (CHCl₃) 3000, 1735, 1690 and 1610 cm⁻¹.

(v) 5(R, S), 6(R, S) Benzyl 6-(1-acetoxyethyl)-3-phenylthio-7-oxo-1-azabicyclo[3,2,0]hept-2-ene-2-carboxylate Cis-4-phenylthiocarbonylmethyl-3-(1-acetoxyethyl)-1-(1-benzyloxycarbonyl-1-triphenylphosphoranylidenemethyl) azetidin-2-one (300 mg) in dry toluene was refluxed for eight hours under argon, using a Dean and Stark apparatus. The solution was evaporated under reduced pressure and the residue was chromatographed on BDH 'Florisil' (200–300 mesh) which gave 5(R, S), 6(R, S) benzyl 6-(1-acetoxyethyl)-3-phenylthio-7-oxo-1-azabicyclo[3,2,0]hept-2-ene-2-carboxylate (25 mg, 14%).

(vi) 5(R, S), 6(S, R) Benzyl 6-(1-acetoxyethyl)-3-phenylthio-7-oxo-1-azabicyclo[3,2,0]hept-2-ene-2-carboxylate Trans-4-allyl-3-(1-acetoxyethyl)-1-(1-benzyloxycarbonyl-1-triphenylphosphoranylidenemethyl)azetidin-2-one was converted to the compound 5(R, S), 6(S, R) benzyl-6-(1-acetoxyethyl)-3-phenylthio-7-oxo-1-azabicyclo[3,2,0]hept-2-ene-2-carboxylate by an analogous route to that outlined in (iii), (iv) and (v).

EXAMPLE 1

5(R,S),6(S,R) Benzyl 3-(Z)-acetamidovinylthio-6-(1-hydroxy-1-methylethyl)-7-oxo-1-azabicyclo[3,2,0]hept-2-ene-2-carboxylate (i) 3(R,S),4(S,R) 4-(Z)-S-Acetamidovinylthiocarbonylmethyl-1-(1-benzyloxycarbonyl-1-triphenylphosphoranylidenemethyl)-3-(1-hydroxy-1-methylethyl)-azetidin-2-one 3(R,S),4(S,R) 1-(1-Benzyloxycarbonyl-1-triphenylphosphoranylidenemethyl)-4-carboxymethyl-3-(1-hydroxy-1-methylethyl)azetidin-2-one (1.61 g) in dry tetrahydrofuran (120 cm³) at 0° and under argon was treated with triethylamine (0.32 g) followed by the dropwise addition of diethylphosphorochloridate (0.56 g) in dry tetrahydrofuran (10 cm³). The mixture was stirred for three hours at room temperature after which lithium (Z)-acetamidovinylthiolate (0.40 g) was added, and the mixture was stirred for a further hour. Filtration and evaporation under reduced pressure gave a crude product which was chromatographed on silica gel 60 (230 mesh) eluting with ethylacetate:methanol mixtures graded from 10:0 to 8:2, and then the product was refiltered through silica gel eluting with ethylacetate to give pure (3R,S),4(S,R) 4-(Z)-S-acetamidovinylthiocarbonylmethyl-1-triphenylphosphoranylidenemethyl)-3-(1-hydroxy-1-methylethyl)-3-(1-hydroxy-1-methylethyl)azetidin-2-one; (0.69 g, 37%).

(ii) 5(R,S),6(S,R) Benzyl 3-(Z)-acetamidovinylthio-1-(1-hydroxy-1-methylethyl)-7-oxo-1-azabicyclo[3,2,0]hept-2-ene-2-carboxylate Part of the product of (i) (670 mg) in dry toluene (700 cm³) was refluxed, under argon, in a Dean and Stark apparatus for 12 hours. The solvent was evaporated under reduced pressure, and the crude product was chromatographed on B.D.H. 'Florisil' (200–300 mesh) eluting with ethyl acetate:petroleum ether 60°–80° mixtures graded from 8:2 to 10:0. This gave 5(R,S),6(S,R) benzyl-3-(Z)-acetamidovinylthio-6-(1-hydroxy-1-methylethyl)-7-oxo-1-azabicyclo [3.2.0]hept-2-ene-2-carboxylate (80 mg, 20%); $\nu_{max}$ (CHCl₃) 3410, 3010, 2980,1775, 1700,1630 cm⁻¹; $\nu_{max}$ (EtOH) 323 nm (14500); δ(CDCl₃) 1.28, 1.37 (6H, 2 s), 1.7–2.0 (1H, br), 2.05 (3H, s), 2.88 (1H, dd, J 9 and 18 Hz), 3.15 (1H, dd, J 9 and 18 Hz), 3.18 (1H, d J 2½ Hz), 4.12 (1H, dt J 2½ and 9 Hz), 5.29 (2H, s), 5.35 (1H, dd, J 6 and 11 Hz), 7.2–7.5 (6H, m), 8.04 (1H, d J 11 Hz), (M⁺ 416.1394, C₂₁H₂₄N₂O₅S required 416.1406). The product crystallised from ethylacetate:petroleum ether; m.p. 134°–135°.

EXAMPLE 2

5(R,S),6(S,R) Benzyl 3-(E)-acetamidovinylthio-6-(1-hydroxy-1-methylethyl)-7-oxo-1-azabicyclo[3,2,0]hept-2-ene-2-carboxylate (i) 4-Allyl-3-(2-hydroxy-2-propyl)azetidin-2-one A solution of 4-allylazetidin-2-one (0.25 g) in dry tetrahydrofuran (25 ml) was stirred at −5° C. under argon and treated with a 2.5 M solution of n-butyllithium in hexane (3.0 ml). A period of 1 hour was allowed for the dianion to form and dry acetone (1.0 ml) was then added. After a further 10 mins. water (5 ml) was added to the reaction mixture, which was then concentrated to about 10 ml in volume. This was extracted with methylene chloride (20 ml), and the organic phase was then dried over sodium sulphate and concentrated. The residue was chromatographed on silica gel 60 (<230 mesh) eluting with ethyl acetate/6-0°–80° petroleum ether 1:1 grading to ethyl acetate to give the cis and trans aldol products. The least polar isomer was cis-4-allyl-3-(2-hydroxy-2-propylazetidin)2-one (0.029 g); m.p. 144° (ethyl acetate/60°–80° petroleum ether). $\nu_{max}$ (CHCl₃) 3400, 2980, 2930, 1745 and 1640 cm⁻¹; δ(CDCl₃) 1.35 (3H, s), 1.51 (3H, s), 2.18 (1H, br), 2.5–2.9 (2H, m), 3.28 (1H, d, J 5 Hz), 3.85 (1H, td J 9 and 5 Hz), 4.9–6.1 (3H, m), and 7.20 (1H, br) (Found: C, 64.2; H, 9.0; N, 8.2%. C₉H₁₅NO₂ requires C, 63.9; H, 8.9 and N, 8.3%). The more polar isomer was trans-4-allyl-3-(2-hydroxy-2-propyl)azetidin-2-one (0.042 g); $\nu_{max}$ (CHCl₃) 3400, 2980, 2930, 1750 and 1640 cm⁻¹, δ(CDCl₃) 1.29 (3H, s), 1.39 (3H, s), 2.41 (3H, br t J 6 Hz), 2.88 (1H, d, J 2 Hz), 3.69 (1, 6d J 6 and 2 Hz), 4.9–5.4 (2H, m), 5.89 (1H, ddt J 18, 9 and 6 Hz), and 6.50 (1H, br).

(ii) The trans isomer prepared as above was converted to the corresponding 1-(1-benzyloxycarbonyl-1-triphenylphosphoranylidenemethyl)azetidin-2-one in conventional manner, and this was converted to the title compound by the methods of description 7.

EXAMPLE 3

5(R,S), 6(S,R)Sodium 3-(E)-2-acetamidoethenylthio-6-(1-hydroxyethyl)-oxo-1-azabicyclo[3,2,0]hept-2-ene-2-carboxylate

(i) Preparation of 7α-(1-p-nitrobenzyloxycarbonyloxyethyl)-2,2'-spirocyclohexyl-8-oxo-3-oxa-1-azabicyclo[4.2.0]octane 7α-(1-Hydroxyethyl)-2-spirocyclohexyl-8-oxo-3-oxa-1-azabicyclo[4.2.0]octane (0.95 g) was dissolved in dry tetrahydrofuran (125 ml) and treated with 2 M-n-BuLi (2.4 ml; 1.2 eqs) under argon at −78°. After 10 minutes p-nitrobenzylchloroformate (1.28 g; 1.5 eqs) in tetrahydrofuran (10 ml) was added and the solution allowed to warm to room temperature over 45 minutes. Water (5 ml) was added and the organic solvent evaporated. The residue was partitioned between ethyl acetate (50 ml) and water (10 ml), dried (MgSO4) and evaporated. Chromatography of the product on Merck Kieselgel 60 (230 mesh) using ethyl acetate/petrol (60°-80°) gave partial separation of the two isomers [Isomer 1, 0.03 g; Mixed fraction, isomer 1+isomer 2, 1.2 g; isomer 2, 0.4 g]. Total Yield 98%.

(ii) Preparation of 3(R,S),4(S,R)-4-(2-Hydroxyethyl)-3-(1-p-nitrobenzyloxycarbonyloxyethyl)azetidin-2-one A quantity of the product from (i) (2.1 g) was dissolved in 10% aqueous acetone (140 ml) containing concentrated sulphuric acid (3 ml) and heated at 50° for three hours. The reaction was cooled to room temperature and water (50 ml) was added. The solution was neutralised with saturated NaHCO3 solution (approx. 100 ml). The acetone was evaporated and the product extracted with ethyl acetate (3×25 ml). The extract was dried (MgSO4), the solvent evaporated and the residue chromatographed on Merck Kieselgel 60 (230 mesh). The product was isolated as a colourless oil (1.2 g; 99%).

The reaction was repeated on the two separate isomers from (i) to provide pure single isomeric products.

(iii) Preparation of 3(R,S), 4(S,R) 4-(3-methoxycarbonyl-2-propen-1-yl)-3-(1-p-nitrobenzyloxycarbonyloxyethyl)azetidin-2-one The product from (ii) (1.2 g) was dissolved in methylene chloride (50 ml) and pyridinium chlorochromate (1.2 g) was added. The reaction was stirred at room temperature for two hours. A further quantity of pyridinium chlorochromate (0.5 g) was added and stirring continued for 1½ hours. The solution was filtered and carbomethoxymethylenephosphorane (1.75 g) was added. The mixture was stirred at room temperature for 1 hour and for 30 minutes at 50°. The solution was applied directly to a silica H (Merck Kieselgel 60 [230 mesh]) Column and eluted with ethyl acetate/petrol 60°-80° to afford the title product as an oil (0.85 g; 60%).

(iv) Preparation of 3(R,S), 4(S,R)-1-(1-hydroxy-1-p-nitrobenzyloxycarbonylmethyl)-4-(3-methoxycarbonyl-2-propen-1-yl)-3-(1-p-nitrobenzyloxycarbonyloxyethyl)azetidin-2 2-one p-Nitrobenzylglyoxylate hydrate (0.75 g) was refluxed in benzene (20 ml) for 1 hour with removal of water (Dean-Stark).

Part of the product from (iii) (0.788 g) was added and the mixture refluxed for nine hours. The solvent was evaporated and the residue dissolved in ethyl acetate and chromatographed on Merck Kiesegel 60 (230 mesh). Elution with 80% ethyl acetate/petrol (60°-80°) gave the product as an oil (0.55 g; 48%).

(v) Preparation of 3(R,S), 4(S,R)-4-(3-methoxycarbonyl-2-propen-1-yl)-3-(1-p-nitrobenzyloxycarbonyloxyethyl)-1-(1-p-nitrobenzyloxycarbonyl-1-triphenylphosphoranylidenemethyl)azetidin-2-one Part of the product from (iv) (0.45 g) in tetrahydrofuran (15 ml) was treated with 2,6 lutidine (0.16 g) followed by thionyl chloride (0.18 g) in tetrahydrofuran (3 ml) at −20°. Stirring was continued at −20° for 20 minutes. The solution was filtered and azeotroped twice with toluene. Dioxan (15 ml) was added followed by lutidine (0.16 g) and triphenylphosphine (0.393 g). The reaction was stirred at room temperature overnight, the solvent removed in vacuo and the residue chromatographed on Merck Kieselgel 60 (230 mesh) to provide the phosphorane as an oil (0.5 g; 80%).

(vi) Preparation of 3(R,S), 4(S,R)-4-carboxymethyl-3-(1-p-nitrobenzyloxycarbonyloxyethyl)-1-(1-p-nitrobenzyloxycarbonyl-1-triphenylphosphoranylidenemethyl)azetidin-2-one Part of the product from (v) (0.42 g) was dissolved in methylene chloride (12 ml) and trifluoroacetic acid (0.4 ml) was added at 0°. The solution was stirred at 0° for ten minutes and cooled to −60°. Ozone was passed into the solution until it went slightly blue and excess ozone was expelled with argon. m-Chloroperbenzoic acid (0.09 g) was added, the mixture allowed to warm to room temperature and stirred overnight. The solvent was evaporated and the residue azeotroped four times with ethyl acetate/toluene. Chromatography of the product on Merck Kieselgel 60 (230 mesh) using ethyl acetate/petrol 60°-80° gave the product as two separable isomers.

(vii) Preparation of 3(R,S), 4(S,R) 4-(E)-Acetamidoethenylthiocarbonylmethyl-3-(1-p-nitrobenzyloxycarbonyloxyethyl)-1-(1-p-nitrobenzyloxycarbonyl-1-triphenylphosphoranylidenemethyl)azetidin-2-one Part of the product from (vi) (0.403 g) was dissolved in dry acetonitrile (5 ml) containing DMF (3 drops). Thionyl chloride (0.06 g) in acetonitrile (1 ml) was added followed by finely-ground E-2-acetamidoethenyl silver thiolate (0.16 g; 1.25 equivalents). The reaction was stirred at room temperature one hour and filtered. The solvent was evaporated and the residue chromatographed on Merck Kieselgel 60 (230 mesh) using petrol (60°-80°)/ethyl acetate as eluent. The product was eluted off the column using ethyl acetate and obtained as a colourless gum which solidified on trituration with ether m.p. 110°-112° (0.25 g; 55%).

(viii) Preparation of 5(R,S), 6(S,R) p-Nitrobenzyl 3-(E)-2-acetamidoethenylthio-6-(1-p-nitrobenzyloxycarbonyloxyethyl)-7-oxo-1-azabicyclo[3,2,0]hept-2-ene-2-carboxylate Part of the product from (vii) (0.15 g) was dissolved in dry toluene and refluxed vigorously under argon for 16 hours. The solvent was evaporated and the residue chromatographed on Merck Kieselgel 60 (230 mesh) using petrol (60°-80°)/ethyl acetate as eluent. The first eluted compound comprised recovered starting thioester phosphorane (0.12 g). The product was then collected as a light yellow oil which solidified on trituration with ether. (0.011 g; 11%, 53% based on recovered phosphorane) $\nu_{max}$ (EtOH) 324 nm, 264 nm $\nu_{max}$ (CHCl$_3$), 3420, 1780, 1745, 1700, 1620, 1610, 1525, 1350, 1340, 1260 cm$^{-1}$. δppm(CDCl$_3$), 1.48(3H, d, J 7.5 Hz), 2.07 (3H, s), 3.04(2H, dd, J 5, 8.5 Hz), 3.47(1H, dd, J=3.0, 4.5 Hz), 4.08(1H, m), 5.00 to 5.60(5H, m including s at 5.25 and ABq at 5.20 and 5.49, J 13.5 Hz), 5.85(1H, d, J 14 Hz), 7.18 (1H, dd, J 11, 14 Hz), 7.55 and 8.20 (4H, ABq, J 8.5 Hz), 7.63 and 8.20 (4H, ABq, J 8.5 Hz), 7.50 (1H).

The recovered phosphorane (0.10 g) was dissolved in dry toluene (125) and refluxed under argon for 48 hours. The solvent was evaporated and the residue chromatographed on Merck Kieselgel 60 (230 mesh) to yield the starting phosphorane (0.65 g) containing a slightly more polar product, the concentration of which had increased following recyclisation. The product (isomer 2) (0.011 g) was collected as a light yellow oil which solidified on trituration with ether.

The phosphorane containing the ether product was rechromatographed twice on Merck Kieselgel 60 (230 mesh) using chloroform/ethanol as eluant to afford the other C-8 isomer (isomer 1) as a gum (0.005 g) $\nu_{max}$ (EtOH) 325 nm, 264 nm, $\nu_{max}$(CHCl$_3$) 3400, 1780, 1750, 1625, 1605, 1525, 1350 cm$^{-1}$: δppm (CDCl$_3$) 1.45 (3H, d, J 7.5 Hz), 2.08 (3H, s), 3.01 (2H, dd, J 4, 8.5 Hz), 3.32 (1H, dd, J 2.5, 8 Hz), 4.10 (1H, m), 5.00 to 5.60 (5H, m, including s at 5.24 and ABq at 5.20 and 5.50 J 13.5 Hz), 5.84 (1H, d, J 14 Hz), 7.20 (1H, dd, J 11, 14 Hz), 7.52 and 8.22 or 8.24 (4H, ABq, J 8.5 Hz), 7.62 and 8.22 or 8.24 (4H, ABq, J 8.5 Hz), 7.50 (1H).

(ix) Preparation of 5(R,S), 6(S,R) sodium 3-(E)-2-acetamidoethenylthio-6-(1S-hydroxyethyl)-7-oxo-1-azabicyclo[3,2,0]hept-2-ene-2-carboxylate Part of the bicyclic azetidinone (isomer 2) from (viii) (0.010 g) was dissolved in 30% aqueous dioxan (1 ml) containing 5% Pd/C (0.018 g) which had previously been hydrogenated for 20 minutes. The solution was hydrogenated at ambient temperature and pressure for two hours. The solution was neutralised with NaHCO$_3$ (0.00014 g) in water (2 ml) and filtered through Kieselguhr. The organic solvent was evaporated and the aqueous phase extracted with ethyl acetate (3×5 ml). Examination of the aqueous phase by u.v. showed it to contain the product $\nu_{max}$(EtOH) 308 nm (H$_2$O) 308 nm.

The concentrations of this compound required to inhibit the growth of the following bacteria are given below.

| Organism | μg ml$^{-1}$ (Microtitre in broth) |
|---|---|
| Escherichia coli O111 | 12.5 |
| Escherichia coli JT 39 | 25 |
| Klebsiella aerogenes A | 25 |
| Proteus mirabilis C977 | 50 |
| Pseudomonas aeruginosa A | 100 |
| Staphylococcus aureus Oxford | 6.2 |
| Staphylococcus aureus Russell | 12.5 |

(x) Preparation of 5(R,S), 6(S,R) Sodium 3-(E)-2-acetamidoethenylthio-6-(1R-hydroxyethyl)-7-oxo-1-azabicyclo[3,2,0]hept-2-ene-2-carboxylate Part of the bicyclic azetidinone (isomer 1) from (viii) was dissolved in 30% aqueous dioxan (1 ml) containing 5% Pd/C (0.008 g) [prehydrogenated 20 minutes]. The solution was hydrogenated at ambient temperature and pressure for two hours, neutralised with NaHCO$_3$ (0.0005 g) and filtered through Kieselguhr. The organic solvent was evaporated and the aqueous phase extracted with ethyl acetate (3 ml). Examination of the aqueous phase by u.v. showed it to contain the product (0.0004 g) $\nu_{max}$ (EtOH) 310 nm (H$_2$O) 308 nm.

The concentrations of this compound required to inhibit the growth of the following bacteria are given below.

| Organism | μg ml$^{-1}$ (Microtitre in broth) |
|---|---|
| Citrobacter freundii E8 | 1.6 |
| Enterobacter cloacae N1 | 1.6 |
| Escherichia coli O111 | 0.8 |
| Escherichia coli JT 39 | 0.8 |
| Klebsiella aerogenes A | 0.8 |
| Proteus mirabilis C977 | 3.1 |
| Proteus morganii I580 | 3.1 |
| Proteus rettgeri VM16 | 3.1 |
| Proteus vulgaris W091 | 3.1 |
| Pseudomones aeruginosa A | 50 |
| Salmonella typhiminim CT10 | 1.6 |
| Serratia marcescens US20 | 1.6 |
| Shigella sennei HB 11967 | 0.8 |
| Staphylococcus aureus Oxford | 0.4 |
| Staphylococcus aureus Russell | 0.8 |
| Staphylococcus aureus 1517 | 12.5 |
| Streptococcus faecalis 1 | 6.2 |
| Escherichia coli ESS | 0.2 |

EXAMPLE 4

5(R,S), 6(R,S)-Benzyl 3-(Z)-2-acetamidoethenylthio)-6-methyl-7-oxo-1-azabicyclo[3.2.0]hept-2-ene-2-carboxylate (i) 3(R,S), 4(R,S)-4-Allyl-1-(1-benzyloxycarbonyl-1-triphenylphosphoranylidenemethyl)-3-methylazetidin-2-one A solution of N-isopropylcyclohexylamine (1.20 g) in dry tetrahydrofuran (10 ml) was stirred in an argon atmosphere at −70° and treated with a 2 M hexane solution of n-butyl lithium (4.8 ml). After 10 minutes a solution of 4-allyl-1-(1-benzyloxycarbonyl-1-triphenylphosphoranylidenemethyl)azetidin-2-one (2.0 g) in tetrahydrofuran (20 ml) was added. After a further 10 minutes the brown anion was quenched by addition of iodomethane (0.72 ml) and the reaction was neutralized 10 minutes later by adition of cetic acid (1.0 g). The reaction mixture was allowed to warm to room temperature, the solvent evaporated, and the residue partitioned between ethyl acetate and brine. The organic phase was separated, dried (Na$_2$SO$_4$) and concentrated in vacuo. Chromatography on silica gel (230), eluting with ethyl acetate/60°-80° petroleum ether 1:1 grading to 3:1 gave 3(R,S), 4(R,S)-4-allyl-1-(1-benzyloxycarbonyl-1-triphenylphosphoranylidenemethyl)-3-methylazetidin-2-one (0.61 g).

(ii) 3(R,S), 4(R,S)-1-(1-Benzyloxycarbonyl-1-triphenylphosphoranylidenemethyl)-4-carboxymethyl-3-methylazetidin-2-one A solution of part of the product from (i) (0.565 g) in dry methylene chloride (50 ml) was cooled to 0° C. and treated with trifluoroacetic acid (2 ml). The stirred solution was cooled to −70° after 10 minutes, and ozone was bubbled through until the reaction mixture just became blue. Excess ozone was blown off with a stream of argon and a solution of m-chloroperbenzoic acid (0.220 g) in methylene chloride (5 ml) was added. The solution was allowed to warm to room temperature and kept overnight before concentration, and re-evaporation twice from toluene. Chromatography on silica gel 60 (<230 mesh) eluting with ethyl acetate grading to ethyl acetate/ethanol 9:1 provided the trifluoroacetic acid salt (0.505 g) of the required product. This was dissolved in chloroform (10 ml) and stirred with basic alumina 90 (activity 1) (0.6 g) for 1½ hours at room temperature. The solution was filtered off and concentrated to give 3(R,S), 4(R,S)-1-(1-benzyloxycarbonyl-1-triphenylphosphoranylidenemethyl)-4-carboxymethyl-3-methylazetidin-2-one (0.406 g) as a colourless foam.

(iii) 3(R,S), 4(R,S)-4-(Z)-S-acetamidoethenylthiocarbonylmethyl-1-(1-benzyloxycarbonyl-1-triphenylphosphoranylidenemethyl)-3-methylazetidin-2-one The product from (ii) (0.406 g) was dissolved in dry acetonitrile (10 ml) and stirred at room temperature under argon. This was treated with dimethylformamide (0.1 ml) followed by thionylchloride (0.096 g) and 2 hours were allowed for the formation of the acid chloride. Silver Z-2-acetamidoethenethiolate (0.245 g) was then added and stirring continued for 1½ hours. The product was filtered and the filtrate concentrated, and chromatographed on silica gel 60 (<230 mesh) eluting with ethylacetate/ethanol 9:1 to give 3(R,S), 4(R,S)-4-(Z)-S-acetamidoethenylthiocarbonylmethyl-1-(1-benzyloxycarbonyl-1-triphenylphosphoranylidenemethyl)-3-methylazetidin-2-one (0.320 g) as a colourless foam.

(iv) 5(R,S), 6(R,S)-Benzyl 3-(Z)-2-acetamidoethenylthio-6-methyl-7-oxo-1-azabicyclo[3.2.0]hept-2-ene-2-carboxylate A solution of part of the product from (iii) (0.100 g) in sodium dried toluene (125 ml), was degassed under reduced pressure, put under an argon atmosphere and was heated under reflux in a Dean and Stark apparatus for 24 hours. The resulting solution was concentrated under reduced pressure and then chromatographed on silica gel 60 (1:1 mixture of 230–400 mesh and 230 mesh) eluting with ethyl acetate grading to ethyl acetate/ethanol 9:1. This afforded recovered phosphorane (0.035) and 5(R,S), 6(R,S)-benzyl 3-(Z)-2-acetamidoethenylthio)-6-methyl-7-oxo-1-azabicyclo[3.2.0]hept-2-ene-2-carboxylate (0.014 g); $\lambda_{max}$ (ethanol) 325 nm: $\nu_{max}$ (CHCl$_3$) 3400, 3000, 2950, 1785, 1705, 1630 and 1560 cm$^{-1}$; $\delta$(CDCl$_3$) 2.03 (1H, br d, J 11 Hz), 2.4–2.8 (6H, m), 4.64 and 4.80 (2H, ABq, J 13 Hz), 4.66 (1H, d, J 7 Hz), 6.17 (1H, td, J 9 and 3H), 6.85 (1H, qd, J 7 and 3 Hz), 6.87 (1H, dd, J 18 and 9 Hz), 7.14 (1H, dd, J 18 and 9 Hz), 7.94 (3H, s) and 8.61 (3H, d, J 7 Hz) (M$^+$ at m/e 372.1137. C$_{19}$H$_{20}$N$_2$O$_4$S requires 372.1143).

EXAMPLE 5

5(R,S), 6(S,R) Benzyl 3-(E)-2-acetamidoethenylthio-6-(1-hydroxyethyl)-7-oxo-1-azabicyclo[3.2.0]hept-2-ene-2-carboxylate (i) 4-Allyl-1-(1-benzyloxycarbonyl-1-triphenylphosphoranylidenemethyl)-3-(1-p-nitrobenzyloxycarbonyloxyethyl)azetidin-2-one A mixture of isomers of 4-allyl-3-(1-hydroxyethyl)-1-(1-benzyloxycarbonyl-1-triphenylphosphoranylidenemethyl)azetidin-2-one and (4.0 g) in dry tetrahydrofuran (200 ml) was treated with 2 M n-butyllithium is n-hexane (4.25 ml) at −78° under argon. After ten minutes p-nitrobenzylchloroformate (2.3 g) in dry tetrahydrofuran (50 ml) was added. The solution was allowed to warm to room temperature and after 45 minutes water (5 ml) was added. The solution was evaporated, partitioned between ethyl acetate and water and the organic phase was separated, dried (Na$_2$SO$_4$) and evaporated to give the crude product. Chromatography of this material on silica gel 60 (230 mesh) eluting with ethylacetate 60°–80° petroleum ether 1:1 gave as a mixture of isomers 4-allyl-1-(1-benzyloxycarbonyl-1-triphenylphosphoranylidenemethyl)-3-(1-p-nitrobenzyloxycarbonyloxyethyl)azetidin-2-one (4.15 g).

(ii) 1-(1-Benzyloxycarbonyl-1-triphenylphosphoranylidenemethyl)-4-carboxymethyl-3-(1-p-nitrobenzyloxycarbonyloxyethyl)azetidin-2-one A quantity of the product of (i) (6.7 g) in dry dichloromethane (250 ml) was treated with trifluoroacetic acid (10.3 g) and the solution was cooled to −78° under argon. Ozone was passed through until the solution darkened. Excess ozone was blown off with argon, and the solution treated with m-chloroperbenzoic acid (1.55 g) in dry dichloromethane (250 ml). The reaction was allowed to warm to room temperature, and was stirred overnight. The solvent was evaporated and the crude product chromatographed on silica gel 60 (230 mesh) eluting with ethylacetate:methanol mixtures graded from 1:0 to 4:1. This gave the trifluoroacetic acid salt of the product which was stirred with basic alumina (5 g) in chloroform for 2 hours. Filtration and evaporation gave as a mixture of isomers 1-(1-benzyloxycarbonyl-1-triphenylphosphoranylidenemethyl)-4-carboxymethyl-3-(1-p-nitrobenzyloxycarbonyloxyethyl)azetidin-2-one (7.58 g).

(iii) 4-(E)-S-Acetamidoethylthiocarbonylmethyl-1-(1-benzyloxycarbonyl-1-triphenylphosphoranylideremethyl)-3-(1-p-nitrobenzyloxycarbonyloxyethyl)azetidin-2-one Part of the product from (ii) (0.61 g) in dry acetonitrile (20 ml) and N,N-dimethylformamide (5 drops) was treated with thionyl chloride (0.10 g) and the solution was stirred at room temperature for 3 hours under argon. Pyridine (0.70 g) was added followed by finely-ground silver (E)-2-acetamido-1-ethenylthiolate (0.28 g), and the mixture was stirred at room temperature for 45 minutes. The mixture was filtered, evaporated and the crude product was chromtographed on silica gel 60 (230 mesh) eluting with ethyl acetate. This gave 4-(E)-S-acetamidoethenylthiocarbonylmethyl-1-(1-benzyloxycarbonyl-1-triphenylphosphoranylidenemethyl)-3-(1-p-nitrobenzyloxycarbonyloxyethyl)azetidin-2-one (0.28 g). $\lambda_{max}$ (CHCl$_3$) 3000, 1750, 1690, 1625, 1610, 1525, 1435, 1350 cm$^{-1}$.

(iv) The product from (iii) was converted to the title compound in a manner analogous to that of Example 3.

EXAMPLE 6

5(R,S), 6(R,S)-p-Nitrobenzyl 3-(Z)-2-acetamidoethenylthio)-6-methyl-7-oxo-1-azabicyclo[3.2.0]hept-2-ene-2-carboxylate

(i) 4-Allyl-1-t-butyldimethylsilylazetidin-2-one

Allylazetidinone (0.22 g) was dissolved in dry N,N-dimethylformamide (5 ml) containing t-butyldimethylsilyl chloride (0.33 g). The solution was cooled to 0° and was treated with triethylamine (0.22 g) in N,N-dimethylformamide (1 ml) over a period of 15 minutes. After a further 15 minutes the solution was poured into ethylacetate/water. The organic phase was separated, washed with dil HCl, brine, dried ($Na_2SO_4$), evaporated, and chromatographed on silica gel 60 (230 mesh) eluting with ethylacetate. This gave 4-allyl-1-t-butyldimethylsilylazetidin-2-one (0.39 g).

(ii) 4-Allyl-1-t-butyldimethylsilyl-3-methylazetidin-2-one

N-Isopropylcyclohexylamine (12.4 g) in dry tetrahydrofuran (300 ml) was treated with 2 M n-butyllithium in n-hexane (44 ml) at −78° under argon. After five minutes 4-allyl-1-t-butyldimethylsilylazetidin-2-one (9.0 g) in dry tetrahydrofuran (100 ml) was added. Thirty minutes later iodomethane (70 ml) was added. The solution was stirred at −78° for 30 minutes and at room temperature for 2 hours, after which acetic acid (5.0 ml) was added. The solution was evaporated and partitioned between ethyl acetate and water. The organic phase was separated, dried ($Na_2SO_4$), evaporated and chromatographed on silica gel 60 (230 mesh) eluting with ethylacetate:petroleum ether (60-80) 1:3 to give as a mixture of two isomers 4-allyl-1-t-butyldimethylsilyl-3-methylazetidin-2-one (8.0 g).

(iii) 4-Allyl-3-methylazetidin-2-one

Part of the isomeric mixture from (ii) (1.20 g) in dry tetrahydrofuran (50 ml) was treated with potassium fluoride (0.45 g) and 18-crown-6 ether (0.07 g). After one hour the solution was partitioned between brine and ethylacetate. The organic phase was separated, dried ($Na_2SO_4$), evaporated and chromatographed on silica gel 60 (<230 mesh) eluting with ethylacetate:hexane 6:4. This separated the trans and cis isomers of 4-allyl-3-methyl azetidin-2-one.

(iv) 3(R,S), 4(R,S)-4-Allyl-1-(1-hydroxy-1-p-nitrobenzyloxycarbonylmethyl)-3-methylazetidin-2-one Part of the trans-methylazetidine from (iii) (150 mg) was dissolved in dry benzene (25 ml) with p-nitrobenzylglyoxylate (550 mg), and the solution was refluxed in a Dean and Stark apparatus for 2 hours. The solution was evaporated and chromatographed on silica gel 60 (230 mesh) eluting with dichloromethane:methanol 98:2 to give 3(R,S), 4(R,S)-4-allyl-1-(1-hydroxy-1-p-nitrobenzyloxycarbonylmethyl)-3-methylazetidin-2-one (350 mg).

(v) 3(R,S), 4(R,S)-4-Allyl-3-methyl-1-(1-p-nitrobenzyloxycarbonyl-1-triphenylphosphoranyldenemethyl)azetidin-2-one Part of the product from (iv) (330 mg) in dry tetrahydrofuran (10 ml) at −5° under argon was treated with 2,6-lutidine (210 mg), followed by thionylchloride (240 mg). After 1 hour the mixture was filtered, evaporated and re-evaporated twice from toluene to give 3(R,S), 4(R,S)-4-allyl-1-(1-chloro-1-p-nitrobenzyloxycarbonylmethyl)-3-methylazetidin-2-one.

This product was dissolved in dry dioxan (10 ml) treated with 2, 6-lutidine (210 mg) and by triphenylphosphine (520 mg) in dry dioxan (10 ml). The solution was stirred overnight at room temperature, filtered, evaporated and chromtogaphed on silica gel 60 (<230 mesh) eluting with ethylacetate:hexane mixtures graded from 1:1 to 1:0. This afforded 3(R,S), 4(R,S)-4-allyl-3-methyl-1-(1-p-nitrobenzyloxycarbonyl-1-triphenylphosphoranylidenemethyl)azetidin-2-one (390 mg).

(vi) 3(R,S), 4(R,S)-4-Carboxymethyl-3-methyl-1-(1-p-nitrobenzyloxycarbonyl-1-triphenylphosphoranylidenemethyl)azetidin-2-one A quantity of the phosphoraneazetidinone product from (v) (11.2 g) in dry dichloromethane (500 ml) was treated with trifluoroacetic acid (70 ml) and was cooled to −78° under argon. Ozone was passed through until the solution darkened. The excess ozone was blown off with argon. The solution was treated with m-chloroperbenzoic acid (3.28 g) in dry dichloromethane (200 ml), allowed to warm to room temperature and left stirring overnight. The solvent was evaporated, and the crude product re-evaporated from toluene, and then chromatographed on silica gel 60 (<230 mesh) eluting with ethyl acetate:methanol mixtures graded from 1:0 to 9:1. This gave the trifluoroacetic acid salt of the acidazetidin-one. This was treated with basic alumina (7 g) in chloroform (100 ml) for 1 hour. Filtration and evaporation gave 3(R,S), 4(R,S)-4-benzyloxycarbonyl-1-triphenylphosphoranylidenemethyl azetidin-2-one (8.07 g); $\nu_{max}$ ($CHCl_3$) 1735, 1610, 1525, 1440, 1350 cm$^{-1}$.

(vii) The product from (vi) was converted to the title compound in a manner analogous to that of example 1.

EXAMPLE 7

5(R,S), 6(S,R) Sodium 3-(E)-2-acetamidoethenylthio-6-(1-phenoxymethylcarbonylethyl)-7-oxo-1-azabicyclo[3.2.0]hept-2-ene-2-carboxylate

(i) Preparation of Trans-3-(1-phenoxyacetoxyethyl)-4-(2-hydroxyethyl)azetidin-2-one

(a) From 7α-(1-phenoxyacetoxyethyl)-2,2-dimethyl-8-oxo-3-oxa-1-azabicyclo[4.2.0]octane 7-(1-phenoxyacetoxyethyl)-2,2-dimethyl-8-oxo-3-oxa-1-azabicyclo[4.2.0]octane (130 mg) was dissolved in 25% aqueous acetone (2 ml) and 5 drops concentrated sulphuric acid was added. The mixture was stirred at room temperature for 10 minutes and neutralised with solid $NaHCO_3$. The organic solvent was evaporated, the aqueous phase diluted with a further quantity of water (5 ml) and extracted with ethyl acetate (3 × 10 ml). The extract was dried ($MgSO_4$) and the solvent evaporated. Chromatography Kieselgel 60 (<230 mesh) yielded the product as an oil (62 mg; 53%).

(b) From 7
-(1-hydroxyethyl)2,2'-spirocyclohexyl-8-oxo-3-oxa-1-
azabicyclo[4.2.0]octane Step 1

7α-(1-Hydroxyethyl)-2,2'-spirocyclohexyl-8-oxo-3-oxa-1-azabicyclo[4.2.0]octane (239 mg) was dissolved in ethyl acetate (20 ml) and cooled to 0°. Phenoxyacetic acid (170 mg) was added followed by dicyclohexylcarbodiimide (275 mg). The mixture was stirred at room temperature for one hour and pyridine (200 mg) added. The reaction was left stirring overnight and filtered. The solution was washed with 20% citric acid (5 ml) and 3% NaHCO$_3$ solution (3×10 ml) and dried over MgSO$_4$. The solvent was evaporated and the residue chromatographed Kieselgel 60 (<230 mesh) to yield the product as a mixture of isomers (0.25 g) which were separable by chromatography on Kieselgel 60 (<230 mesh).

Step 2

Part of the product from step 1 (50 mg) was dissolved in 10% aqueous acetone and concentrated sulphuric acid (5 drops) was added. The mixture was stirred at room temperature for two hours and the solution neutralised with solid NaHCO$_3$. The organic solvent was evaporated, the aqueous phase diluted with water (5 ml) and extracted with ethyl acetate (3×10 ml). The extract was dried over MgSO$_4$ and the solvent evaporated. Chromatography of the resulting oil on Kieselgel 60 (<230 mesh) gave trans-3-(1-phenoxyacetoxyethyl)-4-(2-hydroxyethyl)azetidin-2-one as an oil (12 mg; 30%) identical to the previously described example.

(ii) Preparation of
trans-3-(1-phenoxyacetoxyethyl)-4-(3-methoxycarbonyl-2-propen-1-yl)azetidin-2-one Trans-3-(1-phenoxyacetoxyethyl)-4-(2-hydroxyethyl)azetidin-2-one (mixture of 2 isomers) (29.3 mg) was dissolved in methylene chloride (2 ml) and treated with pyridinium chlorochromate (32 mg). The reaction was stirred at room temperature for three hours and filtered. The filtrate was treated with carbonethoxymethylenetriphenylphosphorane (35 mg) and stirred at room temperature for a further 90 minutes. The solvent was evaporated and the product chromatographed on Kieselgel 60 (230 mesh) to yield trans-3-(1-phenoxyacetoxyethyl)-4-(3-methoxycarbonyl-2-propen-1-yl)acetidin-2-one as an oil (18 mg; 57%); $\nu_{max}$ (CHCl$_3$) 3410, 1765, 1725 cm$^{-1}$. δppm (CDCl$_3$) [mixture of isomers] 1.36 and 1.38 (3H, two doublets, J 6.5 Hz, CHCH$_3$), 2.40 (2H, m, CH$_2$), 2.95 (1H, m, 3C-H), 3.37 (1H, m, 4C-H), 3.67 (3H, s, CO$_2$CH$_3$), and 4.57 and 4.60 (2H, two singlets PhOCH$_2$ for two isomers), 5.27 (1H, m, CH$_3$CH), 5.81 (H, d, J 16 Hz, CH=CHCO$_2$CH$_3$), 6.89 (6H, m, PhOCH$_2$ and CH=CHCO$_2$Me). (Found: M 347.1357. C$_{18}$H$_{21}$NO$_6$ requires M, 347.1357).

(iii) The product from step 2 is converted to the title compound in a manner analogous to that of example 3.

EXAMPLE 8

Following the procedure of the foregoing examples and text the following compounds of the present invention are obtained. (Compounds marked * are also obtained with the cis- configuration about the β-lactam ring)

TABLE 1

| R$_3$ | R$_2$ | R$_1$ |
|---|---|---|
| Me, OH (H); R or S | =/\NHCOMe | Na Phthalidyl |
| Me, OH (H); R or S | /\=/NHCO$_2$Me | Na Phthalidyl |
| Me, OH (H); R or S | /\NHCO$_2$Me | Na Phthalidyl |
| Me, OH (H) | NHCOMe / Me | Na Phthalidyl |
| Me, OCOCH$_2$Ph (H); R or S | /\NHCOMe | Na Phthalidyl |
| Me | /\=/NHCOMe | Na Phthalidyl |
| H | /\NHCOMe | Na Phthalidyl |
| Et | /\=/NHCOMe | Na Phthalidyl |
| H | /\=/NHCOMe | Na Phthalidyl |
| Et | /\NHCOMe | Na Phthalidyl |
| H | /\NHCOMe | Na Phthalidyl |
| Me, OH, Me | =/NHCOMe | Na Phthalidyl |
| Me, OH, Me | /\NHCOMe | CH$_2$Ph |
| Me, OAC (H) | =/NHCOMe | CH$_2$Ph |

TABLE 1-continued

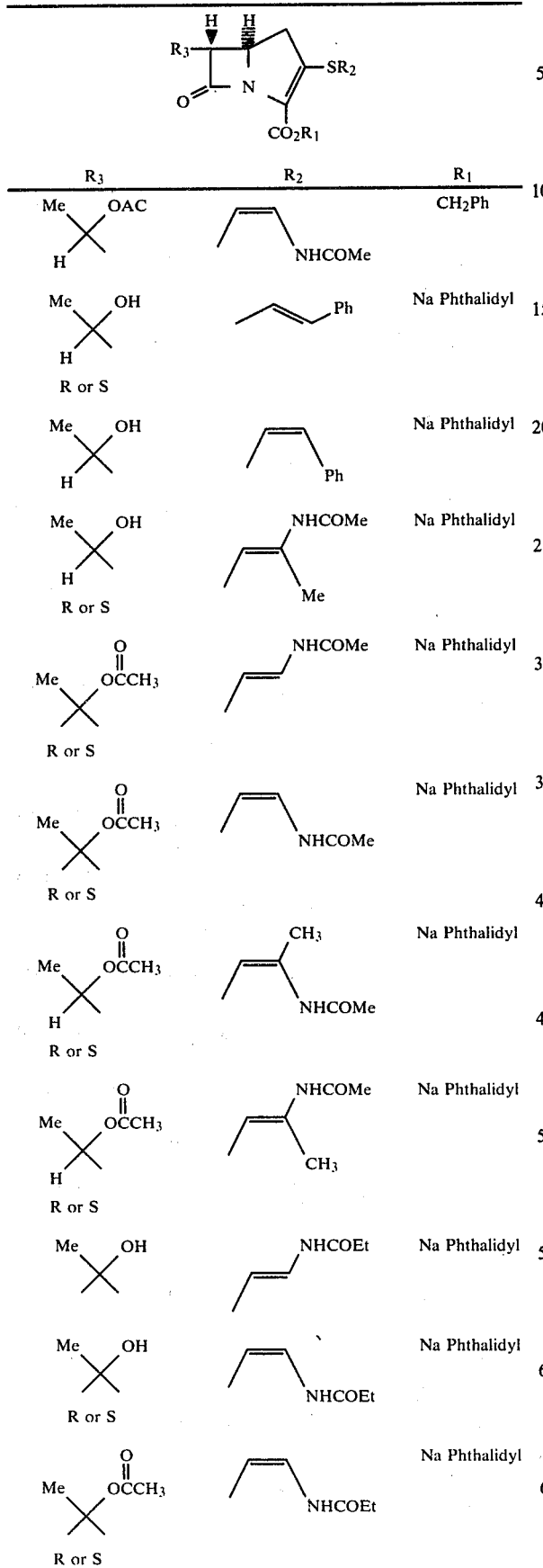

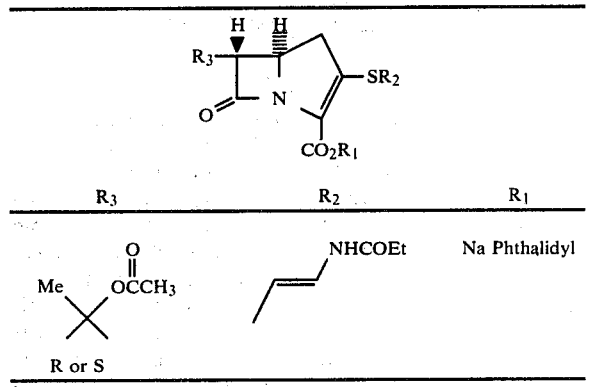

What we claim is:
1. A compound of the formula:

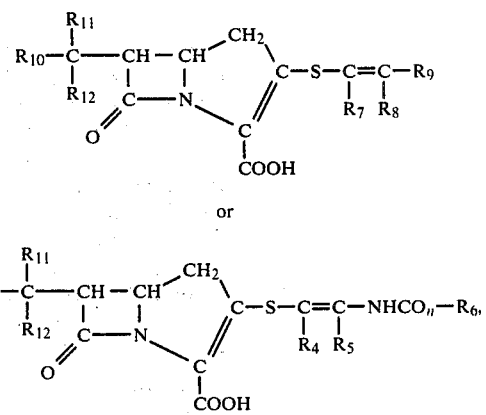

or

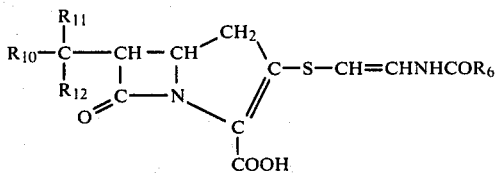

a pharmaceutically acceptable salt thereof or ester thereof, wherein each of $R_4$, $R_5$, $R_7$, $R_8$, $R_{11}$ and $R_{12}$, independently of the others is hydrogen or lower alkyl; $R_6$ is ethyl, n-propyl or isopropyl, phenyl, fluorphenyl, chlorophenyl, bromophenyl or benzyl; $R_9$ is hydrogen, lower alkyl or phenyl; n is 1 or 2; and $R_{10}$ is hydrogen, hydroxy, $R_{13}COO-$ or $R_{13}OCOO-$ in which $R_{13}$ is lower alkyl, phenyl, benzyl, fluorobenzyl, chlorobenzyl, bromobenzyl, lower alkoxybenzyl or nitrobenzyl, and wherein the exocyclic double bond is in the Z configuration.

2. A compound of the formula:

$$R_{10}-\underset{R_{12}}{\overset{R_{11}}{C}}-CH-CH\overset{CH_2}{\underset{C-N}{\diagdown}}C-S-CH=CHNHCOR_6$$
$$O=C\phantom{-N}\underset{COOH}{|}$$

wherein $R_6$ is ethyl, $R_{10}$ is hydrogen, hydroxy, $R_{13}COO-$ or $R_{13}OCOO-$ in which $R_{13}$ is lower alkyl, phenyl, benzyl, fluorobenzyl, chlorobenzyl, bromobenzyl, lower alkoxybenzyl or nitrobenzyl; $R_{11}$ is hydrogen or lower alkyl; $R_{12}$ is hydrogen or lower alkyl and wherein the exocyclic double bond is in the Z configuration.

3. A compound according to claim 2 wherein $R_{11}$ and $R_{12}$, independently of the other, is hydrogen, methyl or ethyl and $R_{10}$ is hydrogen, hydroxy, lower alkyl—COO— or $R_{21}$—OCOO— wherein $R_{21}$ is benzyl, fluorobenzyl, chlorobenzyl, bromobenzyl, lower alkoxybenzyl or nitrobenzyl.

4. A compound according to claim 3 wherein $R_{11}$ is hydrogen, $R_{12}$ is methyl and $R_{10}$ is hydroxy or acetoxy, or a pharmaceutically acceptable salt thereof.

5. A compound according to claim 1 of the formula:

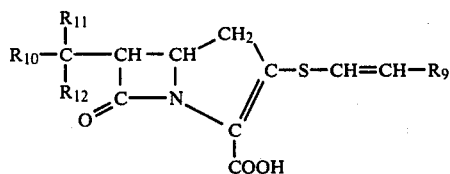

wherein $R_9$ is hydrogen, lower alkyl or phenyl, $R_{10}$ is hydrogen, hydroxy, $R_{13}COO$— or $R_{13}OCOO$— in which $R_{13}$ is lower alkyl, phenyl, benzyl, fluorobenzyl, chlorobenzyl, bromobenzyl, lower alkoxy benzyl or nitrobenzyl, $R_{11}$ is hydrogen or lower alkyl and $R_{12}$ is hydrogen or lower alkyl.

6. A compound according to claim 5 wherein $R_{11}$ and $R_{12}$, independently of the other, is hydrogen, methyl or ethyl and $R_{10}$ is hydrogen, hydroxy, lower alkyl—COO— or $R_{21}$—OCOO— wherein $R_{21}$ is benzyl, fluorobenzyl, chlorobenzyl, bromobenzyl or nitrobenzyl.

7. A compound according to claim 1 in the form of a pharmaceutically acceptable salt.

8. A compound according to claim 7 wherein said salt is the sodium or potassium salt.

9. A compound according to claim 1 in the form of a p-nitrobenzyl or phthalidyl ester.

10. The compound according to claim 1 which is (5R,6S)-sodium 3-(Z)-2-phenylethenylthio-6-(1R)-hydroxyethyl-7-oxo-1-azabicyclo[3.2.0]hept-2-ene-2-carboxylate.

11. The compound according to claim 1 which is (5R,6S) sodium 3-(Z)-2-phenylethenylthio-6-(1S)-hydroxyethyl-7-oxo-1-azabicyclo[3.2.0]hept-2-ene-2-carboxylate.

12. The compound according to claim 1 which is (5R,6S) sodium 3-(Z)-2-propionamidoethenylthio-6(1R)hydroxyethyl-7-oxo-1-azabicyclo[3.2.0]hept-2-ene-2-carboxylate.

13. The compound according to claim 1 which is (5R,6S) sodium 3-(Z)-2-propionamidoethenylthio-6(1S)hydroxyethyl-7-oxo-1-azabicyclo[3.2.0]hept-2-ene-2-carboxylate.

14. The compound according to claim 1 which is (5R,6S) sodium 3-(Z)-2-propionamidoethenylthio-6(1R)acetoxyethyl-7-oxo-1-azabicyclo[3.2.0]hept-2-ene-2-carboxylate.

15. The compound according to claim 1 which is (5R,6S) sodium 3-(Z)-2-propionamidoethenylthio-6(1S)acetoxyethyl-7-oxo-1-azabicyclo[3.2.0]hept-2-ene-2-carboxylate.

16. A pharmaceutical composition useful for treating bacterial infections in humans and domestic animals which comprises an antibacterially effective amount of a compound selected from the group consisting of:

(5R,6S) sodium 3-(Z)-2-acetamidoprop-1-enylthio-6(1R)-hydroxyethyl-7-oxo-1-azabicyclo[3.2.0-]hept-2-ene-2-carboxylate, (5R,6S) sodium 3-(Z)-2-acetamidoprop-1-enylthio-6(1S)-hydroxyethyl-7-oxo-1-azabicyclo[3.2.0]hept-2-ene-2-carboxylate, (5R,6S) sodium 3-(Z)-2-acetamidoprop-1-enylthio-6(1R)acetoxyethyl]-7-oxo-1-azabicyclo[3.2.0]hept-2-ene-2-carboxylate, (5R,6S) sodium 3-(Z)-2-acetamidoprop-1-enylthio-6(1S)acetoxyethyl-7-oxo-1-azabicyclo[3.2.0]hept-2-ene-2-carboxylate, (5R,6S) phthalidyl 3-(Z)-2-acetamidoprop-1-enylthio-6(1R)-hydroyethyl-7-oxo-1-azabicyclo[3.2.0]hept-2-ene-2-carboxylate, (5R,6S) phthalidyl 3-(Z)-2-acetamidoprop-1-enylthio-6(1S)-hydroxyethyl-7-oxo-1-azabicyclo[3.2.0]hept-2-ene-2-carboxylate, (5R,6S) phthalidyl 3-(Z)-2-acetamidoprop-1-enylthio-6(1R)acetoxyethyl-7-oxo-1-azabicyclo[3.2.0]hept-2-ene-2-carboxylate and (5R,6S) phthalidyl 3-(Z)-2-acetamidoprop-1-enylthio-6(1S)acetoxyethyl-7-oxo-1-azabicyclo[3.2.0]hept-2-ene-2-carboxylate, in combination with a pharmaceutically acceptable carrier.

17. A compound selected from the group consisting of:

(5R, 6S) sodium 3-(Z)-2-acetamidoprop-1-enylthio-6(1R)-hydroxyethyl-7-oxo-1-azabicyclo[3.2.0-]hept-2-ene-2-carboxylate, (5R,6S) sodium 3-(Z)-2-acetamidoprop-1-enylthio-6(1S)-hydroxyethyl-7-oxo-1-azabicyclo[3.2.0]hept-2-ene-2-carboxylate, (5R,6S) sodium 3-(Z)-2-acetamidoprop-1-enylthio-6(1R) acetoxyethyl-7-oxo-1-azabicyclo[3.2.0]hept-2-ene-2-carboxylate, (5R,6S) sodium 3-(Z)-2-acetamidoprop-1-enylthio-6(1S)acetoxyethyl-7-oxo-1-azabicyclo[3.2.0]hept-2-ene-2-carboxylate, (5R,yS) phthalidyl 3-(Z)-2-acetamidoprop-1-enylthio-6(1R)-hydroxyethyl-7-oxo-1-azabicyclo[3.2.0]hept-2-ene-2-carboxylate, (5R,6S) phthalidyl 3-(Z)-2-acetamidoprop-1-enylthio-6(1S)-hydroxyethyl-7-oxo-1-azabicyclo[3.2.0]hept-2-ene-2-carboxylate, (5R, 6S) phthalidyl 3-(Z)-2-acetamidoprop-1-enylthic-6(1R)acetoxyethyl-7-oxo-1-azabicyclo[3.2.0-]hept-2-ene-2-carboxylate and (5R,6S)phthalidyl 3-(Z)-2-acetamidoprop-1-enylthio-6(1S)acetoxyethyl-7-oxo-1-azabicyclo[3.2.0]hept-2-ene-2-carboxylate.

18. A pharmaceutical composition useful for treating bacterial infections in humans and domestic animals which comprises an antibacterially effective amount of a compound of the formula:

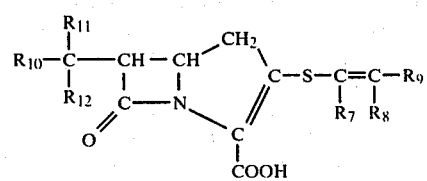

-continued

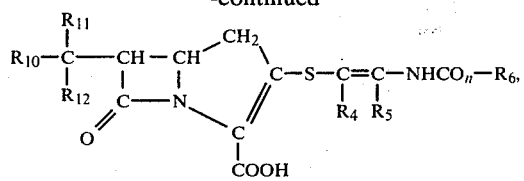

a pharmaceutically acceptable salt thereof or ester thereof, wherein each of $R_4$, $R_5$, $R_7$, $R_8$, $R_{11}$ and $R_{12}$, independently of the others is hydrogen or lower alkyl; $R_6$ is ethyl, n-propyl or isopropyl, phenyl, fluorphenyl, chlorophenyl, bromophenyl or benzyl; $R_9$ is hydrogen, lower alkyl or phenyl; n is 1 or 2; and $R_{10}$ is hydrogen, hydroxy, $R_{13}COO-$ or $R_{13}OCOO-$ in which $R_{13}$ is lower alkyl, phenyl, benzyl, fluorobenzyl, chlorobenzyl, bromobenzyl, lower alkoxybenzyl or nitrobenzyl, and wherein the exocyclic double bond is in the Z configuration, in combination with a pharmaceutically acceptable carrier.

19. A composition according to claim 18 wherein the compound is of the formula:

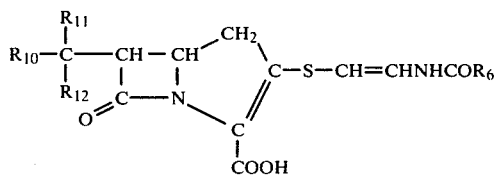

wherein $R_6$ is ethyl, $R_{10}$ is hydrogen, hydroxy, $R_{13}COO-$ or $R_{13}OCOO-$ in which $R_{13}$ is lower alkyl, phenyl, benzyl, fluorobenzyl, chlorobenzyl, bromobenzyl, lower alkoxybenzyl or nitrobenzyl; $R_{11}$ is hydrogen or lower alkyl; $R_{12}$ is hydrogen or lowr alkyl.

20. A composition according to claim 19 wherein $R_{11}$ and $R_{12}$, independently of the other, is hydrogen, methyl or ethyl and $R_{10}$ is hydrogen, hydroxy, lower alkyl—COO— or $R_{21}$—OCOO— wherein $R_{21}$ is benzyl, fluorobenzyl, chlorobenzyl, bromobenzyl, or nitrobenzyl.

21. A composition according to claim 20 wherein $R_{11}$ is hydrogen, $R_{12}$ is methyl and $R_{10}$ is hydroxy or acetoxy, or a pharmaceutically acceptable salt thereof.

22. A pharmaceutical composition useful for treating bacterial infections in humans and domestic animals which comprises an antibacterially effective amount of the formula:

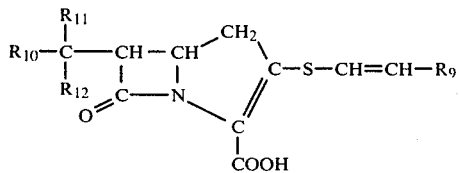

wherein $R_9$ is hydrogen, lower alkyl or phenyl, $R_{10}$ is hydrogen, hydroxy, $R_{13}COO-$ or $R_{13}OCOO-$ in which $R_{13}$ is lower alkyl, phenyl, benzyl, fluorobenzyl, chlorobenzyl, bromobenzyl, lower alkoxybenzyl or nitrobenzyl, $R_{11}$ is hydrogen or lower alkyl and wherein the exocyclic double bond is in the Z configuration and $R_{12}$ is hydrogen or lower alkyl, in combination with a pharmaceutically acceptable carrier.

23. A composition according to claim 22 wherein $R_{11}$ and $R_{12}$, independently of the other, is hydrogen, methyl or ethyl and $R_{10}$ is hydrogen, hydroxy, lower alkyl—COO— or $R_{21}$—OCOO— wherein $R_{21}$ is benzyl, fluorobenzyl, chlorobenzyl, bromobenzyl, or nitrobenzyl.

24. A composition according to claim 18 wherein the compound is the form of a pharmaceutically acceptable salt.

25. A composition according to claim 24 wherein said salt is the sodium or potassium salt.

26. A composition according to claim 18 wherein the compound is in the form of a p-nitrobenzyl or phthalidyl ester.

27. A composition according to claim 18 wherein the compound is (5R,6S)-sodium 3-(Z)-2-phenylethenylthio-6-(1R)-hydroxyethyl-7-oxo-1-azabicyclo[3.2.0-]hept-2-ene-2-carboxylate.

28. A composition according to claim 18 wherein the compound is (5R,6S) sodium 3-(Z)-2-phenylethenylthio-6-(1S)-hydroxyethyl-7-oxo-1-azabicyclo[3.2.0-]hept-2-ene-2-carboxylate.

29. A composition according to claim 18 wherein the compound is (5R,6S) sodium 3-(Z)-2-propionamidoethenylthio-6-(1R)hydroxyethyl-7-oxo-1-azabicyclo[3.2.0]hept-2-ene-2-carboxylate.

30. A composition according to claim 18 wherein the compound is (5R,6S) sodium 3-(Z)-2-propionamidoethenylthio-6-(1S)hydroxyethyl-7-oxo-1-azabicyclo[3.2.0]hept-2-ene-2-carboxylate.

31. A composition according to claim 18 wherein the compound is (5R,6S) sodium 3-(Z)-2-propionamidoethenylthio-6-(1R)acetoxyethyl-7-oxo-1-azabicyclo[3.2.0]hept-2-ene-2-carboxylate.

32. A composition according to claim 18 wherein the compound is (5R,6S) sodium 3-(Z)-2-propionamidoethenylthio-6-(1S)acetoxyethyl-7-oxo-1-azabicyclo[3.2.0]hept-2-ene-2-carboxylate.

33. A composition according to claim 22 in injectible administration form.

34. A method of treating bacterial infections in humans and domestic animals which comprises administering to a human or domestic animal in need thereof of an antibacterially effective amount of a compound of the formula:

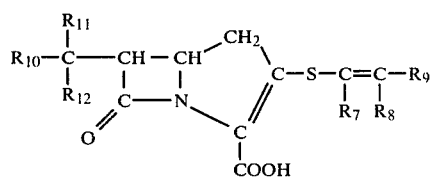

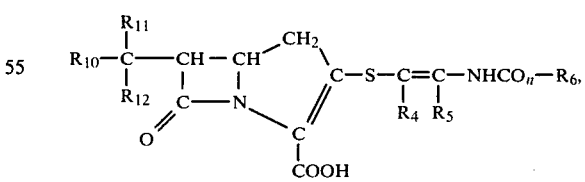

a pharmaceutically acceptable salt thereof or ester thereof, wherein each of $R_4$, $R_5$, $R_7$, $R_8$, $R_{11}$ and $R_{12}$, independently of the others is hydrogen or lower alkyl; $R_6$ is ethyl, n-propyl or isopropyl, phenyl fluorphenyl, chlorophenyl, bromophenyl or benzyl; $R_9$ is hydrogen, lower alkyl or phenyl; n is 1 or 2; and $R_{10}$ is hydrogen, hydroxy, $R_{13}COO-$ or $R_{13}OCOO-$ in which $R_{13}$ is lower alkyl, phenyl, benzyl, fluorobenzyl, chlorobenzyl, bromobenzyl, lower alkoxybenzyl or nitrobenzyl, and wherein the exocyclic double bond is in the Z configuration, in combination with a pharmaceutically acceptable carrier.

35. A method according to claim 34 wherein the compound is of the formula:

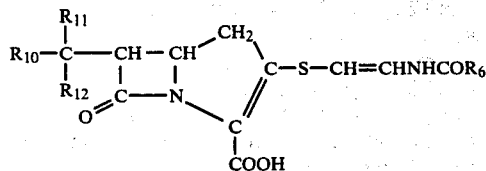

wherein $R_6$ is ethyl, $R_{10}$ is hydrogen, hydroxy, $R_{13}COO-$ or $R_{13}OCOO-$ in which $R_{13}$ is lower alkyl, phenyl, benzyl, fluorobenzyl, chlorobenzyl, bromobenzyl, lower alkoxybenzyl or nitrobenzyl; $R_{11}$ is hydrogen or lower alkyl; $R_{12}$ is hydrogen or lower alkyl.

36. A method according to claim 35 wherein $R_{11}$ and $R_{12}$, independently of the other, is hydrogen, methyl or ethyl and $R_{10}$ is hydrogen, hydroxy, lower alkyl—COO— or $R_{21}$—OCOO— wherein $R_{21}$ is benzyl, fluorobenzyl, chlorobenzyl, bromobenzyl, or nitrobenzyl.

37. A method according to claim 36 wherein $R_{11}$ is hydrogen, $R_{12}$ is methyl and $R_{10}$ is hydroxy or acetoxy, or a pharmaceutically acceptable salt thereof.

38. A method of treating bacterial infections in humans and domestic animals which comprises administering to a human or domestic animal in need thereof an antibacterially effective amount of a compound of the formula:

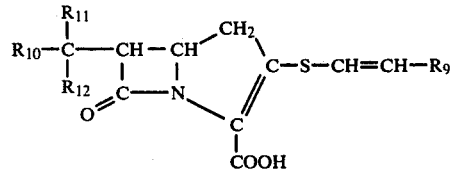

wherein $R_9$ is hydrogen, lower alkyl or phenyl, $R_{10}$ is hydrogen, hydroxy, $R_{13}COO-$ or $R_{13}OCOO-$ in which $R_{13}$ is lower alkyl, phenyl, benzyl, fluorbenzyl, chlorobenzyl, bromobenzyl, lower alkoxybenzyl, or nitrobenzyl, $R_{11}$ is hydrogen or lower alkyl and wherein the exocyclic double bond is in the Z configuration and $R_{12}$ is hydrogen or lower alkyl, in combination with a pharmaceutically acceptable carrier.

39. A method according to claim 38 wherein $R_{11}$ and $R_{12}$, independently of the other, is hydrogen, methyl or ethyl and $R_{10}$ is hydrogen, hydroxy, lower alkyl—COO— or $R_{21}$—OCOO— wherein $R_{21}$ is benzyl, fluorobenzyl, chlorobenzyl, bromobenzyl, or nitrobenzyl.

40. A method according to claim 34 wherein the compound is the form of a pharmaceutically acceptable salt.

41. A method according to claim 40 wherein said salt is the sodium or potassium salt.

42. A method according to claim 34 wherein the compound is in the form of a p-nitrobenzyl or phthalidyl ester.

43. A method according to claim 34 wherein the compound is (5R,6S)-sodium 3-(Z)-2-phenylethenylthio-6-(1R)-hydroxyethyl-7-oxo-1-azabicyclo[3.2.0]hept-2-ene-2-carboxylate.

44. A method according to claim 34 wherein the compound is (5R,6S) sodium 3-(Z)-2-phenylethenylthio-6-(1S)-hydroxyethyl-7-oxo-1-azabicyclo[3.2.0]hept-2-ene-2-carboxylate.

45. A method according to claim 34 wherein the compound is (5R,6S) sodium 3-(Z)-2-propionamidoethenylthio-6(1R)hydroxyethyl-7-oxo-1-azabicyclo[3.2.0]hept-2-ene-2-carboxylate.

46. A method according to claim 34 wherein the compound is (5R,6S) sodium 3-(Z)-2-propionamidoethenylthio-6(1S)hydroxyethyl-7-oxo-1-azabicyclo[3.2.0]hept-2-ene-2-carboxylate.

47. A method according to claim 34 wherein the compound is (5R,6S) sodium 3-(Z)-2-propionamidoethenylthio-6(1R)acetoxyethyl-7-oxo-1-azabicyclo[3.2.0]hept-2-ene-2-carboxylate.

48. A method according to claim 34 wherein the compound is (5R,6S) sodium 3-(Z)-2-propionamidoethenylthio-6(1S)acetoxyethyl-7-oxo-1-azabicyclo[3.2.0]hept-2-ene-2-carboxylate.

49. The compound according to claim 1 which is (5R,6S) phthalidyl 3-(Z)-2-phenylethenylthio-6-(1S)-hydroxyethyl-7-oxo-1-azabicyclo[3.2.0]hept-2-ene-2-carboxylate.

50. The compound according to claim 1 which is (5R,6S) phthalidyl 3-(Z)-2-phenylethenylthio-6-(1S)-hydroxyethyl-7-oxo-1-azabicyclo[3.2.0]hept-2-ene-2-carboxylate.

51. The compound according to claim 1 which is (5R,6S) phthalidyl 3-(Z)-2propionamidoethenylthio-6(1R)hydroxyethyl-7-oxo-1-azabicyclo[3.2.0]hept-2-ene-2-carboxylate.

52. The compound according to claim 1 which is (5R,6S) phthalidyl 3-(Z)-2-propionamidoethenylthio-6(1S)hydroxyethyl-7-oxo-1-azabicyclo[3.2.0]hept-2-ene-2-carboxylate.

53. The compound according to claim 1 which is (5R,6S) phthalidyl 3-(Z)-2-propionamidoethenylthio-6(1R)acetoxyethyl-7-oxo-1-azabicyclo[3.2.0]hept-2-ene-2-carboxylate.

54. The compound according to claim 1 which is (5R,6S) phthalidyl 3-(Z)-2-propionamidoethenylthio-6(1S)acetoxyethyl-7-oxo-1-azabicyclo[3.2.0]hept-2-ene-2-carboxylate.

55. A composition according to claim 18 wherein the compound is (5R,6S) phthalidyl 3-(Z)-2-phenylethenylthio-6-(1R)-hydroxyethyl-7-oxo-1-azabicyclo[3.2.0]hept-2-ene-2-carboxylate.

56. A composition according to claim 18 wherein the compound is (5R,6S) phthalidyl 3-(Z)-2-phenylethenylthio-6-(1S)-hydroxyethyl-7-oxo-1-azabicyclo[3.2.0]hept-2-ene-2-carboxylate.

57. A composition according to claim 18 wherein the compound is (5R,6S) phthalidyl 3-(Z)-2-propionamidoethenylthio-6(1R)hydroxyethyl-7-oxo-1-azabicyclo[3.2.0]hept-2-ene-2-carboxylate.

58. A composition according to claim 18 wherein the compound is (5R,6S) phthalidyl 3-(Z)-2-propionamidoethenylthio-6(1S)hydroxyethyl-7-oxo-1-azabicyclo[3.2.0]hept-2-ene-2-carboxylate.

59. A composition according to claim 18 wherein the compound is (5R,6S) phthalidyl 3-(Z)-2-propionamidoethenylthio-6(1R)acetoxyethyl-7-oxo-1-azabicyclo[3.2.0]hept-2-ene-2-carboxylate.

60. A composition according to claim 18 wherein the compound is (5R,6S) phthalidyl 3-(Z)-2-propionamidoethenylthio-6(1S)acetoxyethyl-7-oxo-1-azabicyclo[3.2.0]hept-2-ene-2-carboxylate.

61. A method according to claim 34 wherein the compound is (5R,6S) phthalidyl 3-(Z)-2-phenylethenylthio-6-(1R)-hydroxyethyl-7-oxo-1-azabicyclo[3.2.0]hept-2-ene-2-carboxylate.

62. A method according to claim 34 wherein the compound is (5R,6S) phthalidyl 3-(Z)-2-phenylethenylthio-6-(1S)-hydroxyethyl-7-oxo-1-azabicyclo[3.2.0]hept-2-ene-2-carboxylate.

63. A method according to claim 34 wherein the compound is (5R,6S) phthalidyl 3-(Z)-2-propionamidoethenylthio-6(1S)hydroxyethyl-7-oxo-1-azabicyclo[3.2.0]hept-2-ene-2-carboxylate.

64. A method according to claim 34 wherein the compound is (5R,6S) phthalidyl 3-(Z)-2-propionamidoethenylthio-6(1R)acetoxyethyl-7-oxo-1-azabicyclo[3.2.0]hept-2-ene-2-carboxylate.

65. A method according to claim 34 wherein the compound is (5R,6S) phthalidyl 3-(Z)-2-propionamidoethenylthio-6(1S)acetoxyethyl-7-oxo-1-azabicyclo[3.2.0]hept-2-ene-2-carboxylate.

66. A method of treating bacterial infections in humans and domestic animals which comprises administering to a human or domestic animal in need thereof an antibacterially effective amount of a compound selected from the group consisting of:

(5R,6S) sodium 3-(Z)-2-acetamidoprop-1-enylthio-6(1R)hydroxyethyl-7-oxo-1-azabicyclo[3.2.0]hept-2-ene-2-carboxylate, (5R,6S) sodium 3-(Z)-2-acetamidoprop-1-enylthio-6(1S)hydroxyethyl-7-oxo-1-azabicyclo[3.2.0]hept-2-ene-2-carboxylate, (5R,6S) sodium 3-(Z)-2-acetamidoprop-1-enylthio-6(1R)acetoxyethyl-7-oxo-1-azabicyclo[3.2.0]hept-2-ene-2-carboxylate, (5R,6S) sodium 3-(Z)-2-acetamidoprop-1-enylthio-6(1S)acetoxyethyl-7-oxo-1-azabicyclo[3.2.0]hept-2-ene-2-carboxylate, (5R,6S) phthalidyl 3-(Z)-2-acetamidoprop-1-enylthio-6(1R)hydroxyethyl-7-oxo-1-azabicyclo[3.2.0]hept-2-ene-2-carboxylate, (5R,6S) phthalidyl 3-(Z)-2-acetamidoprop-1-enylthio-6(1S)hydroxyethyl-7-oxo-1-azabicyclo[3.2.0]hept-2-ene-2-carboxylate, (5R,6S) phthalidyl 3-(Z)-2-acetamidoprop-1-enylthio-6(1R)acetoxyethyl-7-oxo-1-azabicyclo[3.2.0]hept-2-ene-2-carboxylate and (5R,6S) phthalidyl 3-(Z)-2-acetamidoprop-1-enylthio-6(1S)acetoxyethyl-7-oxo-1-azabicyclo[3.2.0]hept-2-ene-2-carboxylate, in combination with a pharmaceutically acceptable carrier.

67. A method according to claim 34 wherein the compound is (5R$_1$6S) phthalidyl 3-(Z)-2-propionamidoethenylthio-6 (1R)hydroxyethyl-7-oxo-1-azabicyclo[3.2.0]hept-2-3n3-2-carboxylate.

68. A composition according to claim 18 in oral administration form.

69. A composition according to claim 18 in injectible administration form.

70. A composition according to claim 22 in oral administration form.

71. A method according to claim 34 wherein the administration is oral.

72. A method according to claim 34 wherein the administration is by injection.

73. A method according to claim 44 wherein the administration is oral.

74. A method according to claim 44 wherein the administration is by injection.

* * * * *